United States Patent
Chang et al.

(10) Patent No.: US 7,030,124 B2
(45) Date of Patent: Apr. 18, 2006

(54) METHOD OF TREATING DEPRESSION WITH DELTA RECEPTOR AGONIST COMPOUNDS

(75) Inventors: Kwen-Jen Chang, Chapel Hill, NC (US); William Pendergast, Durham, NC (US); Peter J. Gengo, Raleigh, NC (US)

(73) Assignee: Ardent Pharmaceuticals, Inc., Durham, NC (US)

( * ) Notice: Subject to any disclaimer, the term of this patent is extended or adjusted under 35 U.S.C. 154(b) by 170 days.

(21) Appl. No.: 10/282,411

(22) Filed: Oct. 29, 2002

(65) Prior Publication Data

US 2003/0144299 A1 Jul. 31, 2003

Related U.S. Application Data

(60) Provisional application No. 60/337,887, filed on Nov. 2, 2001, provisional application No. 60/340,084, filed on Oct. 29, 2001.

(51) Int. Cl.
*A61K 31/495* (2006.01)
*A61K 31/496* (2006.01)

(52) U.S. Cl. .............................. 514/255.04; 514/253.01
(58) Field of Classification Search ........... 514/255.04, 514/253.01
See application file for complete search history.

(56) References Cited

U.S. PATENT DOCUMENTS

| | | | |
|---|---|---|---|
| 5,552,404 A | 9/1996 | Chang et al. ............... 514/255 |
| 5,574,159 A | 11/1996 | Chang et al. ............... 544/396 |
| 5,658,908 A | 8/1997 | Chang et al. ............... 514/252 |
| 5,681,830 A | 10/1997 | Chang et al. ................ 514/85 |
| 5,807,858 A * | 9/1998 | Chang et al. .......... 514/255.04 |
| 5,854,249 A | 12/1998 | Chang et al. ............... 514/255 |
| 5,985,880 A | 11/1999 | Chang et al. ............... 514/255 |
| 6,046,200 A | 4/2000 | Tortella et al. ............. 514/250 |
| 6,200,978 B1 | 3/2001 | Maw et al. ............. 514/254.05 |
| 6,300,332 B1 * | 10/2001 | Chang et al. .......... 514/255.04 |
| 2002/0022624 A1 | 2/2002 | Dinnell et al. ............ 514/228.2 |
| 2002/0052007 A1 | 5/2002 | Chang ........................ 435/7.1 |

FOREIGN PATENT DOCUMENTS

WO    WO 02/094794    11/2002

OTHER PUBLICATIONS

Broom et al. "Nonpeptidic opioid receptor agonists reduce immobility in the forced swim assay in rats." Neurophychopharmacology 2002—vol. 26, No. 6, 744-755.

Cottney et al. "Synthesis of novel analogues of the delta opioid ligand SNC-80 using rem resin." Bioorganic & Medicinal Chemistry 9 (1999) 1323-1328.

Lopez et al. "Exploring the structure—activity relationships of [1-(4-tert-butyl-3'-hydroxy)benzhydryl-4-benzylpiperazines] (SL-3111), a high affinity and selective opioid receptor nonpeptide agonist ligand." J. Med. Chem.1999, 42, 5359-5368.

Calderon et al. "Probes for narcotic receptor mediated phenomena." J. Med. Chem. 1997, 40, 695-704.

Comer et al. "Convulsive effects of systemic administration of the delta opioid agonist BW272U86 in mice." The Journal of Phar. and Exp. Ther. vol. 267, No. 2, 888-895. 1993.

M. Scott Furness, et al., Probes for Narcotic Receptor-Mediated Phenomena. 27[1] Synthesis and Pharmacological Evaluation of Selective L-Opioid Receptor Agonists from 4-[(ã KR)-K-(2S,5R)-4-Substituted—,5-dimethyl-1-piperazinyl-3-methoxybenzyl]-N,N-diethylbenzamides and Their Enantiomers, J. Med.Chem., 2000, 43, 3193-3196.

* cited by examiner

*Primary Examiner*—Phyllis G. Spivack
(74) *Attorney, Agent, or Firm*—Steven J. Hultquist; Intellectual Property/Technology Law

(57) ABSTRACT

Methods for treatment of depression or other affective mood disorders, such as bipolar manic depression or seasonal affective disorder, are disclosed by administration to a subject suffering or susceptible to same, of therapeutically effective diarylpiperazine compounds as herein described.

8 Claims, No Drawings

METHOD OF TREATING DEPRESSION WITH DELTA RECEPTOR AGONIST COMPOUNDS

CROSS-REFERENCE TO RELATED APPLICATIONS

This application claims priority from U.S. Provisional Patent Application No. 60/340,084 filed on Oct. 29, 2001 and U.S. Provisional Patent Application No. 60/337,887 filed on Nov. 2, 2001.

BACKGROUND OF THE INVENTION

1. Field of the Invention

The present invention relates to compositions and methods of treatment of depression or other affective mood disorders or pathological mental and/or emotional states, by administration to a subject suffering or susceptible to same, of delta opioid receptor agonist compound(s), optionally in combination with other agents.

2. Description of the Related Art

Depression is a difficult mental disorder to treat. Patients having such a disorder are often reluctant to seek the medical attention necessary to diagnose the disorder. Such reluctance is often related to the patient's fear of the stigma associated with seeking psychiatric help or to the patient's feeling of worthlessness associated with depression. Moreover, once the patients seek competent psychiatric help, it is difficult to successfully treat the disorder through a psychoanalytic approach alone.

In the Diagnostic and Statistical Manual of Mental disorders, Fourth Edition, (DSM IV) published by the American Psychiatric Association, depressive disorders are classified under mood disorders and are divided into three types: major depressive disorder, dysthymic disorder and depressive disorder not otherwise specified. Major depressive disorder and dysthymic disorder are differentiated based on chronicity, severity and persistence. In major depression, the depressed mood must be present for two weeks. In dysthymic disorder, the depressed mood must be present for two weeks. In dysthymic disorder the depressed mood must be present most days over a period of two years.

Usually, major depressive disorder is characterized by its sharp contrast to usual functioning. A person with a major depressive episode can be functioning and feeling normal and suddenly develop severe symptoms of depression. By contrast, a person with dysthymic disorder has chronic depression with less severe symptoms than major depression.

In an effort to treat depression, a variety of antidepressant compositions have been developed. Among these are the selective serotonin reuptake inhibitors (SSRI), such as sertraline (registered trademark ZOLOFT®—Pfizer), fluoxetine (registered trademark PROZAC®—Eli Lilly), paroxetine (trade name PAXIL®—Glaxo Smith Kline), and fluvoxamine (trade name LUVOX™). Other examples of antidepressant compositions include tricyclic antidepressants such as those sold under the registered trademark ELAVIL™ (Merck, Sharpe and Dohme); aminoketone antidepressants such as bupropion; and lithium, a metal used to treat bipolar disorder. However, these drugs are potent, often generating problematic side effects such as lethargy, clouded thinking, a lack of ability to concentrate, and sexual dysfunction. Often, these drugs take about six to eight weeks to exhibit any desirable therapeutic effects. This time period can be prolonged when the correct drug or combinations of drugs has to be determined, by trial and error before any therapeutic effects are observed. Furthermore, current research suggests that many of these drugs produce undesirable physiological side and it is also unknown how these drugs may affect pediatric and adolescent patients.

Therefore, what is needed is an effective, pharmacologically-based treatment for depression. It would also be desirable to have a treatment that potentiates the action and reduces the side effects of known compositions used in the treatment of depression. Such a method of treatment is lacking in the prior art.

SUMMARY OF THE INVENTION

The present invention relates in one aspect to a method of combating a mood disorder in a subject experiencing or susceptible to same, comprising administering to said subject an effective amount of a therapeutic composition comprising a diarylmethylpiperazine compound of the general formula:

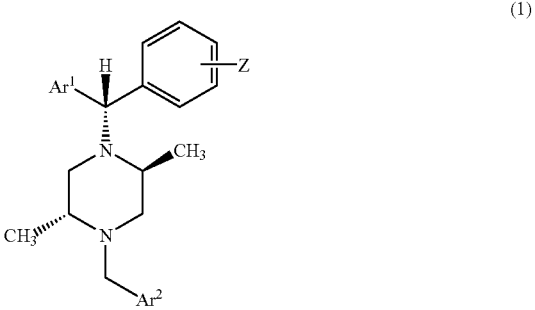

(1)

wherein:

Ar$^1$ is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent R$^1$, Y is selected from the group consisting of:

hydrogen;

halogen;

$C_1$–$C_6$ alkyl, $C_2$–$C_6$ alkenyl, $C_2$–$C_6$ alkynyl;

$C_1$–$C_6$ haloalkyl;

$C_1$–$C_6$ alkoxy;

$C_3$–$C_6$ cycloalkoxy;

sulfides of the formula SR$^8$ where R$^8$ is $C_1$–$C_6$ alkyl, $C_2$–$C_6$ alkenyl, $C_2$–$C_6$ alkynyl, $C_3$–$C_6$ cycloalkyl, arylalkyl having a $C_5$–$C_{10}$ aryl moiety and an $C_1$–$C_6$ alkyl moiety, or $C_5$–$C_{10}$ aryl;

sulfoxides of the formula SOR$^8$ where R$^8$ is the same as above;

sulfones of the formula SO$_2$R$^8$ where R$^8$ is the same as above;

nitrile;

$C_1$–$C_6$ acyl;

alkoxycarbonylamino (carbamoyl) of the formula NHCO$^2$R$^8$ where R$^8$ is the same as above;

carboxylic acid, or an ester, amide, or salt thereof;

aminomethyl of the formula $CH_2NR^9R^{10}$ where $R^9$ and $R^{10}$ may be the same or different, and may be hydrogen, $C_1$–$C_6$ alkyl, $C_2$–$C_6$ alkenyl, $C_2$–$C_6$ alkynyl, $C_2$–$C_6$ hydroxyalkyl, $C_2$–$C_6$ methoxyalkyl, $C_3$–$C_6$ cycloalkyl, or $C_5$–$C_{10}$ aryl, or $R^9$ and $R^{10}$ together may form a ring of 5 or 6 atoms, the ring atoms selected from the group consisting of N and C;

carboxamides of the formula $CONR^9R^{10}$ where $R^9$ and $R^{10}$ are the same as above, or $C_2$–$C_{30}$ peptide conjugates thereof; and sulfonamides of the formula $SO_2NR^9R^{10}$ where $R^9$ and $R^{10}$ are the same as above;

$R^1$ is hydrogen, halogen, or $C_1$–$C_4$ alkyl, $C_2$–$C_4$ alkenyl, $C_1$–$C_4$ alkynyl;

Z is selected from the group consisting of hydrogen, hydroxyl, halogen and alkoxy;

$Ar^2$ is a 5 or 6-member carbocyclic or heterocyclic aromatic ring with atoms selected from the group consisting of carbon, nitrogen, oxygen and sulfur, and having on a carbon atom thereof a substituent X X is selected from the group consisting of hydrogen, halogen (fluorine, bromine, chlorine, iodine), hydroxy and alkoxy; or a pharmaceutically acceptable ester or salt thereof.

Preferably, the Z group is positioned on the third carbon.

While the compounds of the present invention are described hereinafter with primary reference to diarylmethylpiperazines and benzyl derivatives thereof, including their respective ester and salt forms, it will be recognized that the methods of the invention for treatment of various mental disorders may include use of a wide variety of diarylmethylpiperazines wherein the piperazinyl ring has an arylalkyl substituent, e.g., arylalkyl having $C_1$–$C_6$ alkyl or aryl moieties, wherein the aryl is a $Ar^2$ is a 5 or 6-member carbocyclic or heterocyclic aromatic ring with atoms selected from the group consisting of carbon, nitrogen, oxygen and sulfur, and having on a carbon atom thereof a substituent X, where X is selected from the group consisting of hydrogen, halogen (fluorine, bromine, chlorine, iodine), hydroxy and alkoxy.

Another aspect of the invention relates to a method of combating a mood disorder in a subject experiencing or susceptible to same, comprising administering to said subject an effective amount of a therapeutic composition comprising at least one compound selected from the group consisting of:

(i)
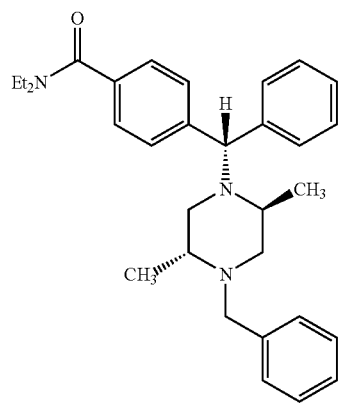

(ii)
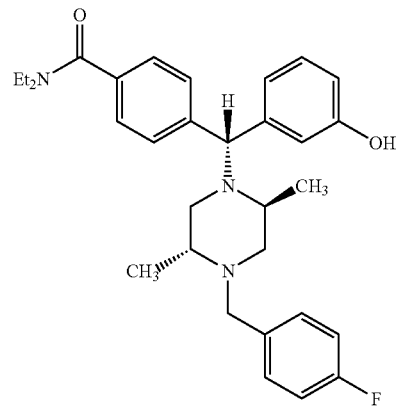

(iii)
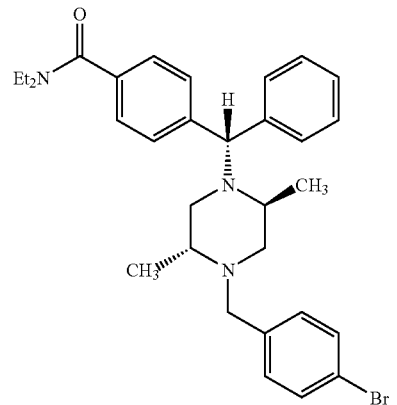

(iv)
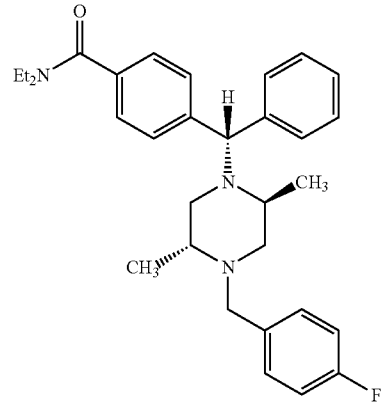

(v)
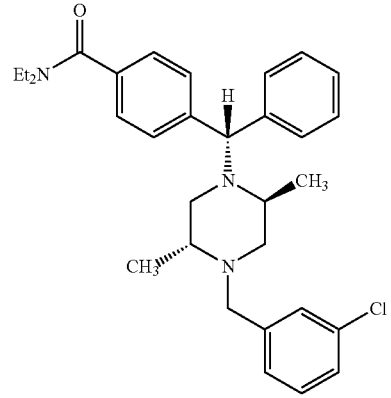

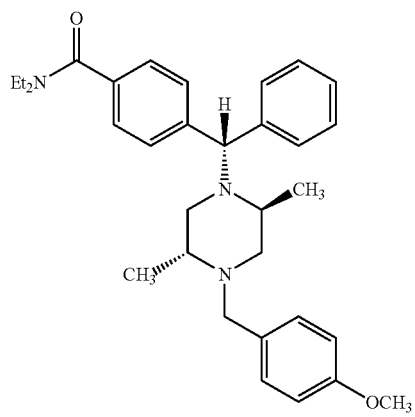
(vi)
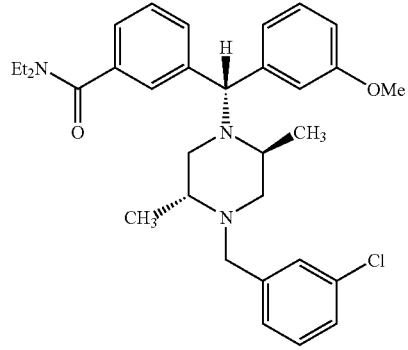
(x)
(vii)
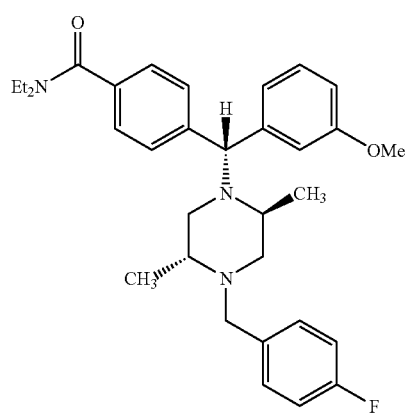
(xi)
(viii)
(xii)
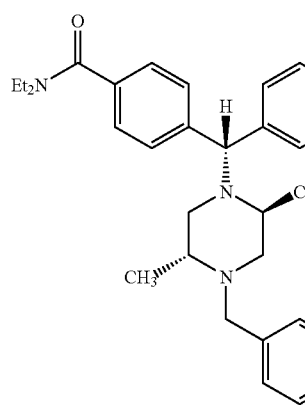
(ix)
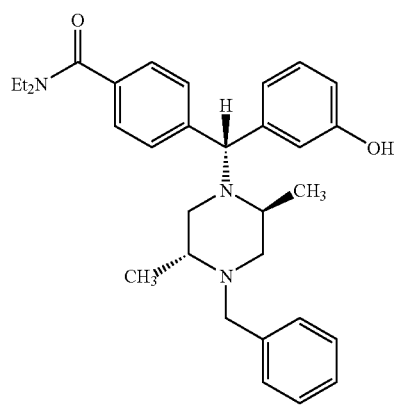
(xiii)

(xiv)
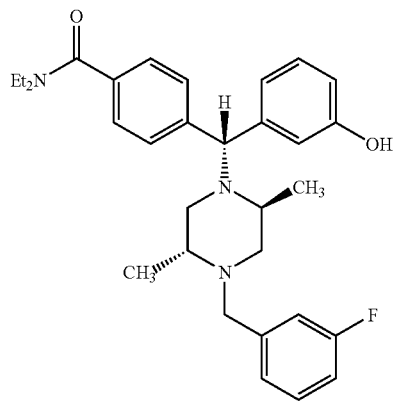
(xv)
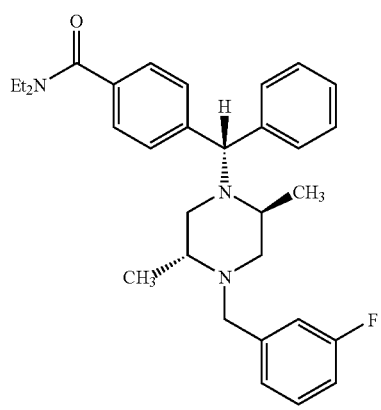
(xvi)
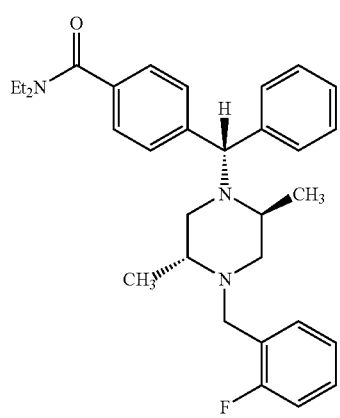
(xvii)
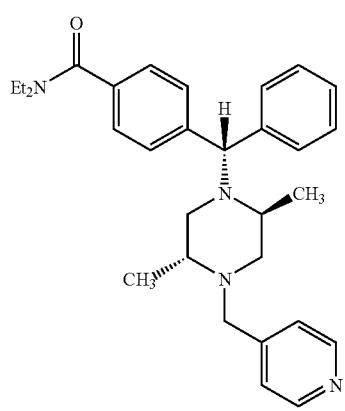
(xviii)
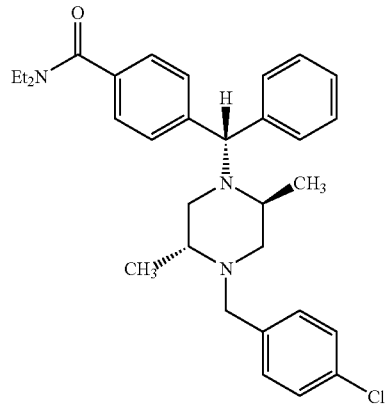
(xix)
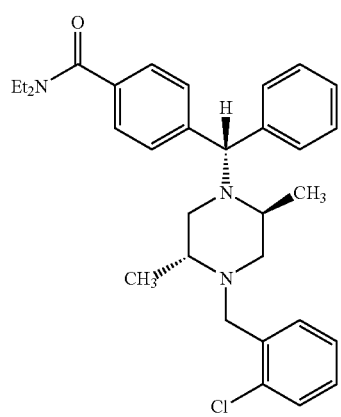
(xx)
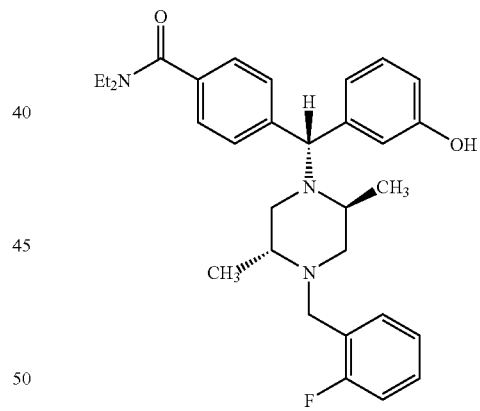
(xxi)
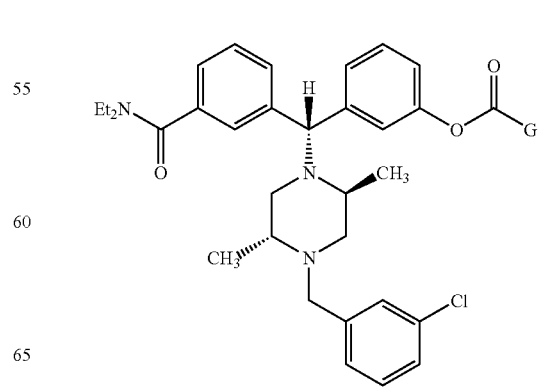

where G=O-alkyl, N(alkyl)₂, and any other pharmaceutically acceptable esters thereof, and pharmaceutically acceptable esters and salts of the foregoing compounds.

The therapeutic compositions may be administered by any suitable administrative mode, e.g., an administration modality selected from the group consisting of oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

A still further aspect of the present invention relates to a method of combating a mood disorder in a subject experiencing or susceptible to same, comprising administering to said subject an effective amount of a therapeutic composition comprising at least one compound selected from the group consisting of:

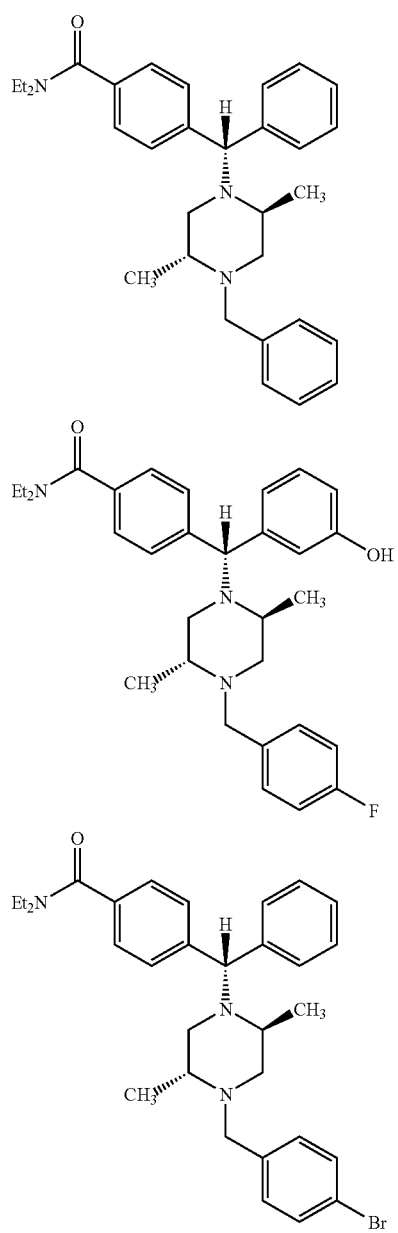

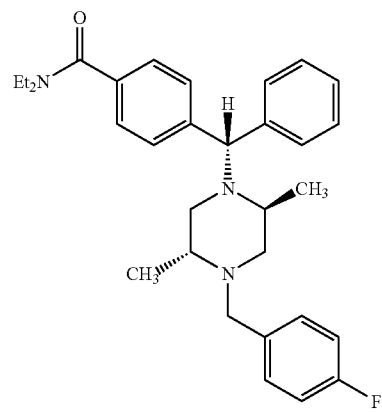

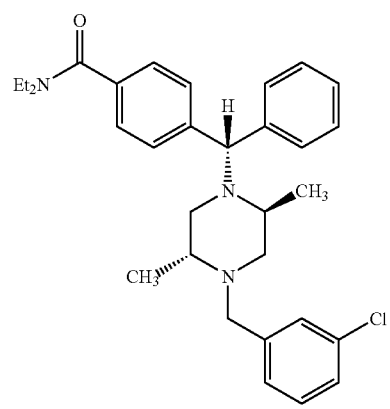

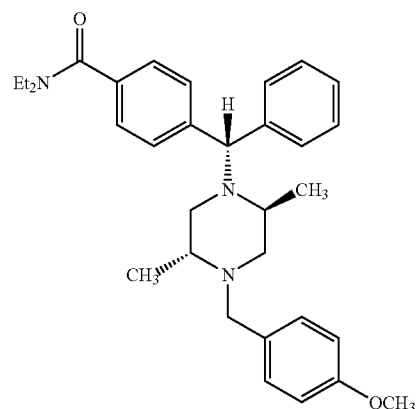

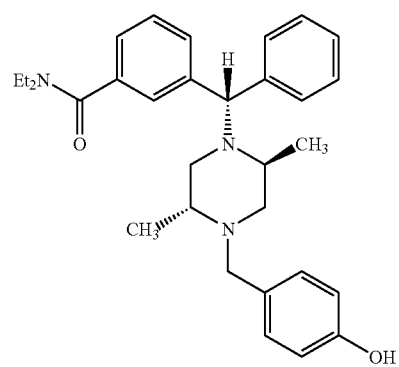

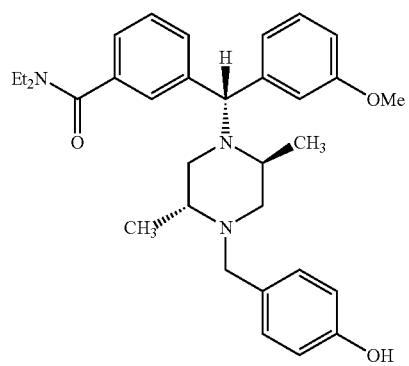
(viii)
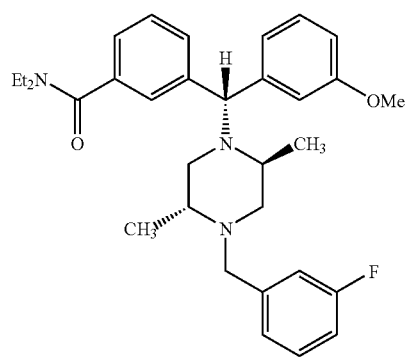
(ix)
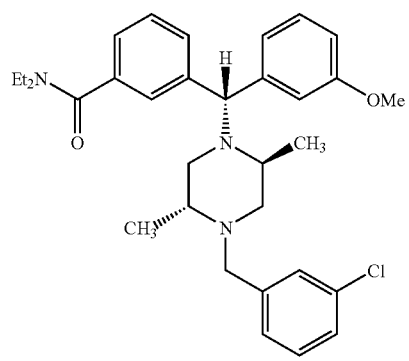
(x)
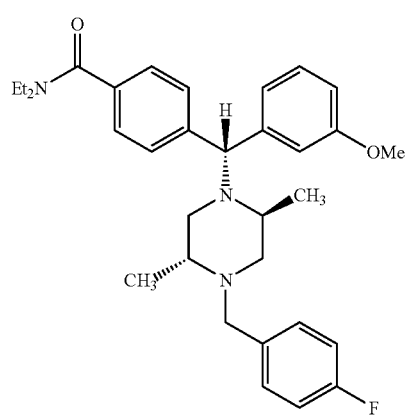
(xi)
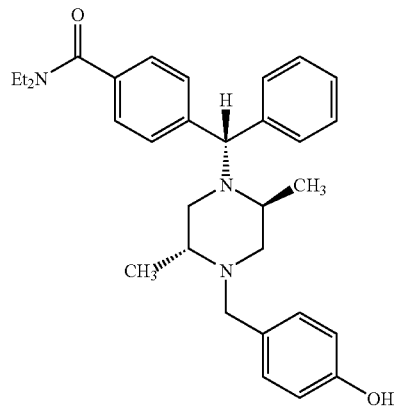
(xii)
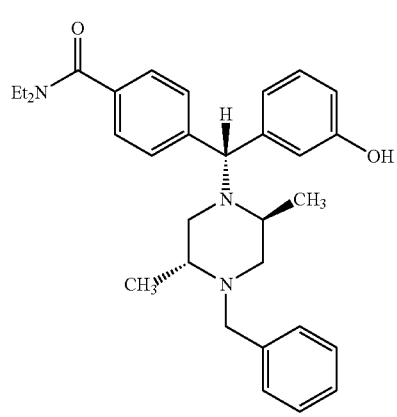
(xiii)
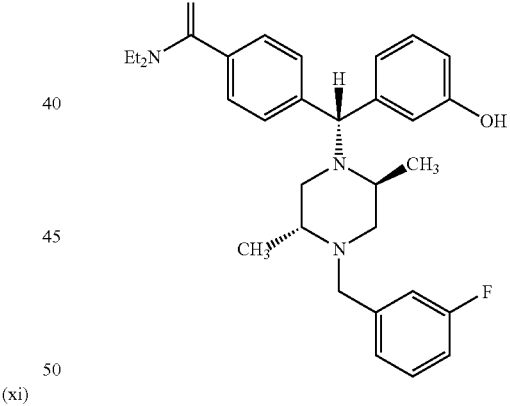
(xiv)
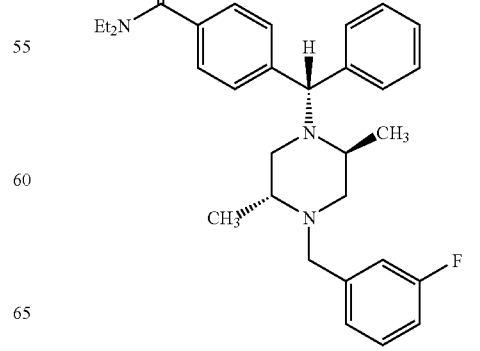
(xv)

-continued

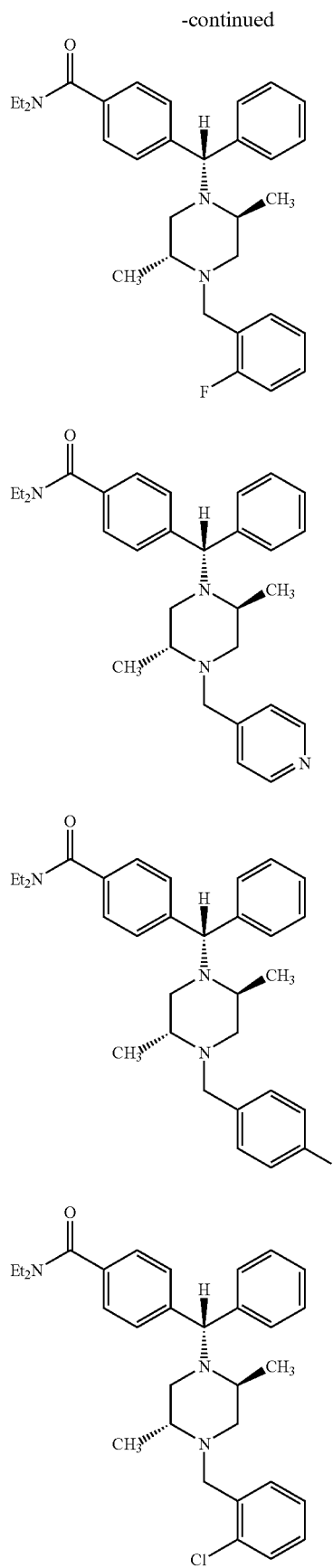

(xvi)

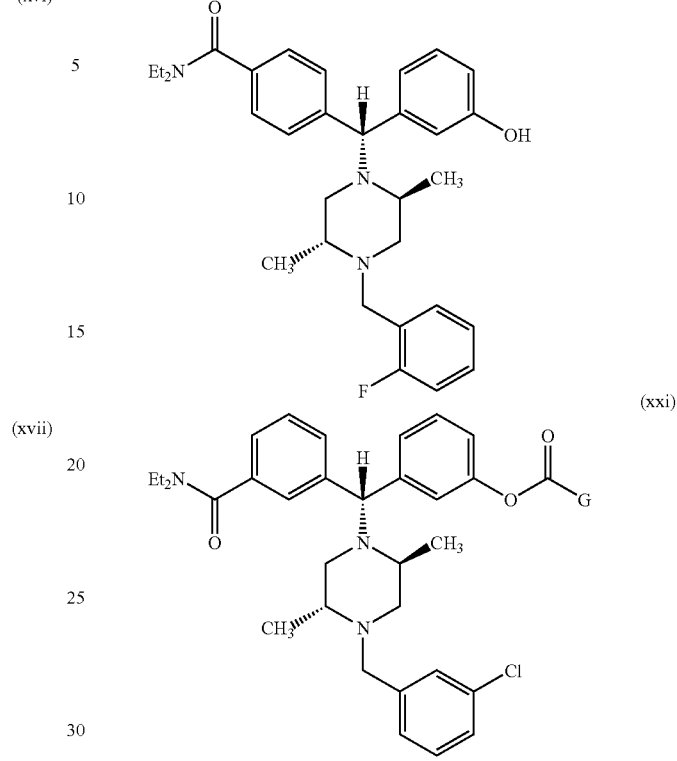

(xvii)

(xviii)

(xix)

(xx)

(xxi)

where G=O-alkyl, N(alkyl)₂, and any other pharmaceutically acceptable esters thereof, and pharmaceutically acceptable esters and salts of the foregoing compounds;

and another mood disorder-combating agent.

The mood disorder-combating agent may be of any suitable type, and may include, without limitation, tricyclic antidepressants, MAO inhibitors, 5-HT agonists and antagonists, aminoketones, serotonin reuptake inhibitors and adrenergic reuptake inhibitors. In one specific embodiment according to the invention, wherein another mood disorder-combating agent is employed in the administered therapeutic composition, such other mood disorder-combating agent is not a diarylmethylpiperazine compound and/or a delta opioid receptor agonist.

An additional aspect of the invention relates to a composition for combating a mood disorder in a subject experiencing or susceptible to same, comprising at least one compound selected from the group consisting of (i)

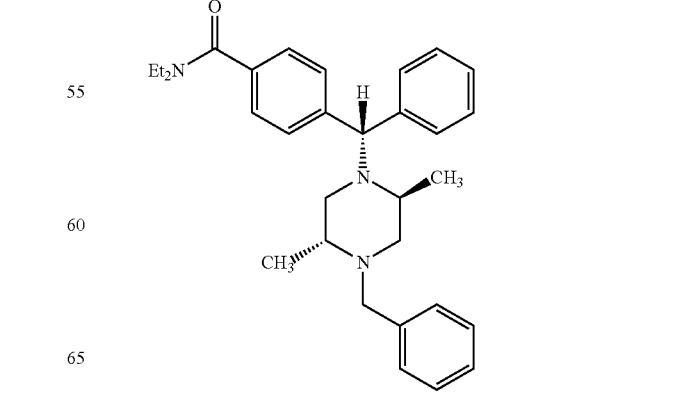

(ii)
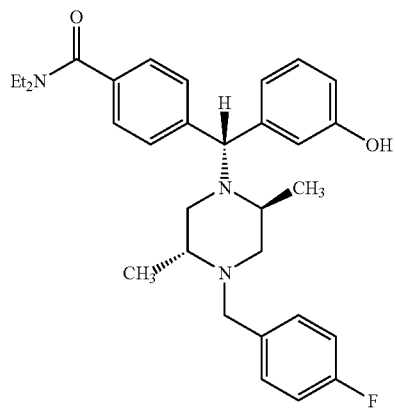
(iii)
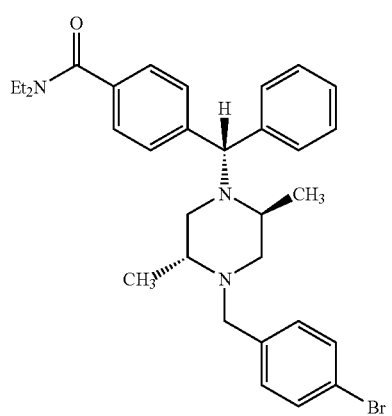
(iv)
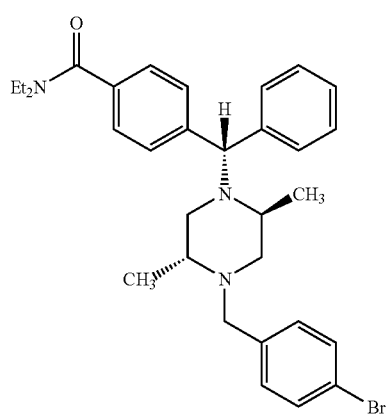
(v)
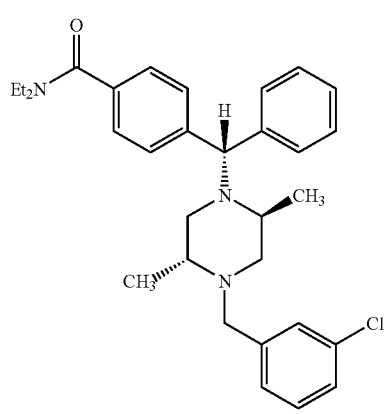
(vi)
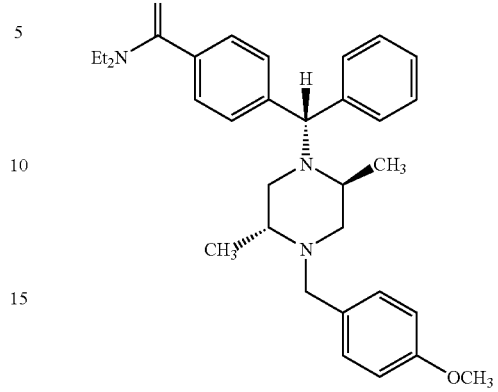
(vii)
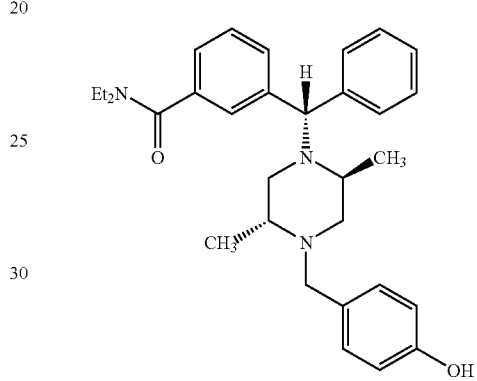
(viii)
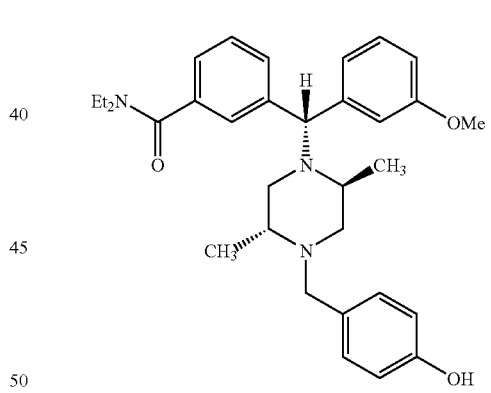
(ix)
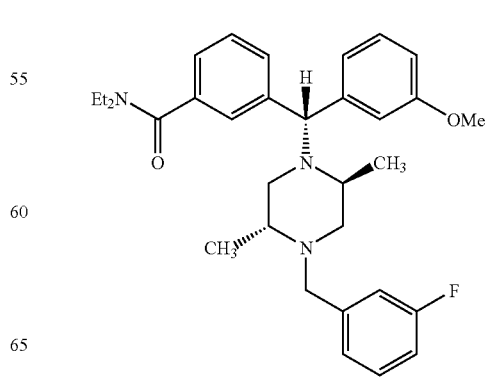

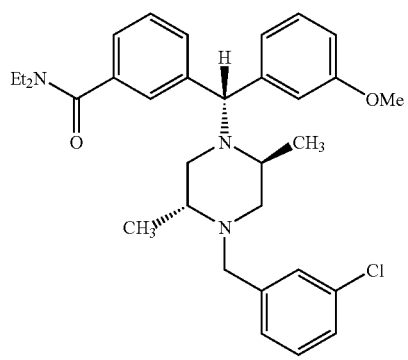
(x)
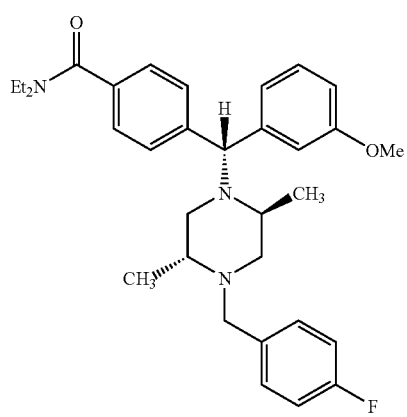
(xi)
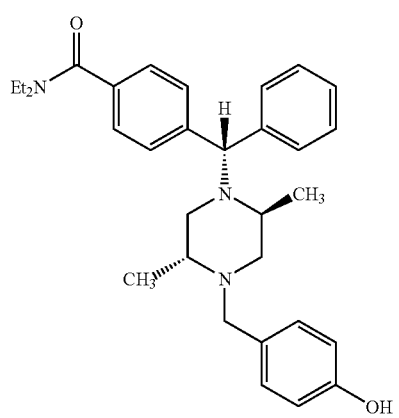
(xii)
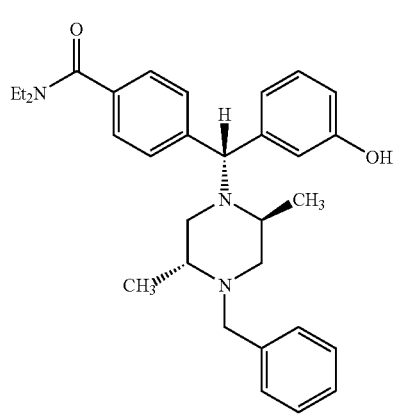
(xiii)
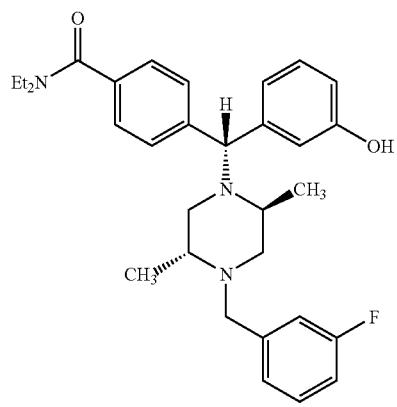
(xiv)
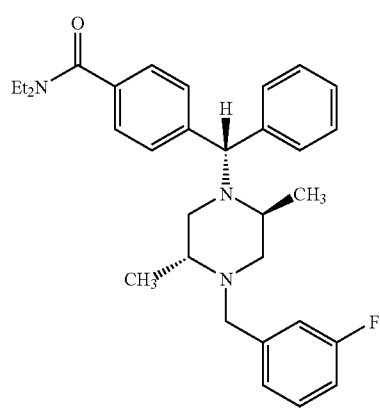
(xv)
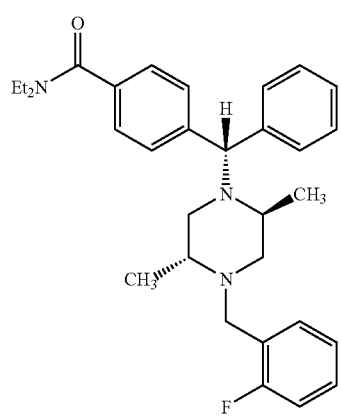
(xvi)
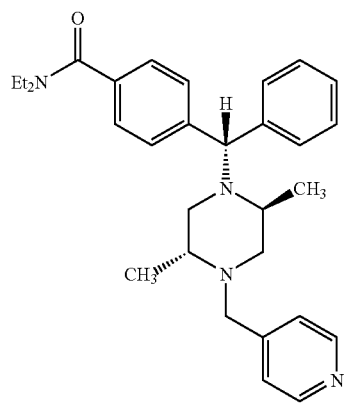
(xvii)

-continued

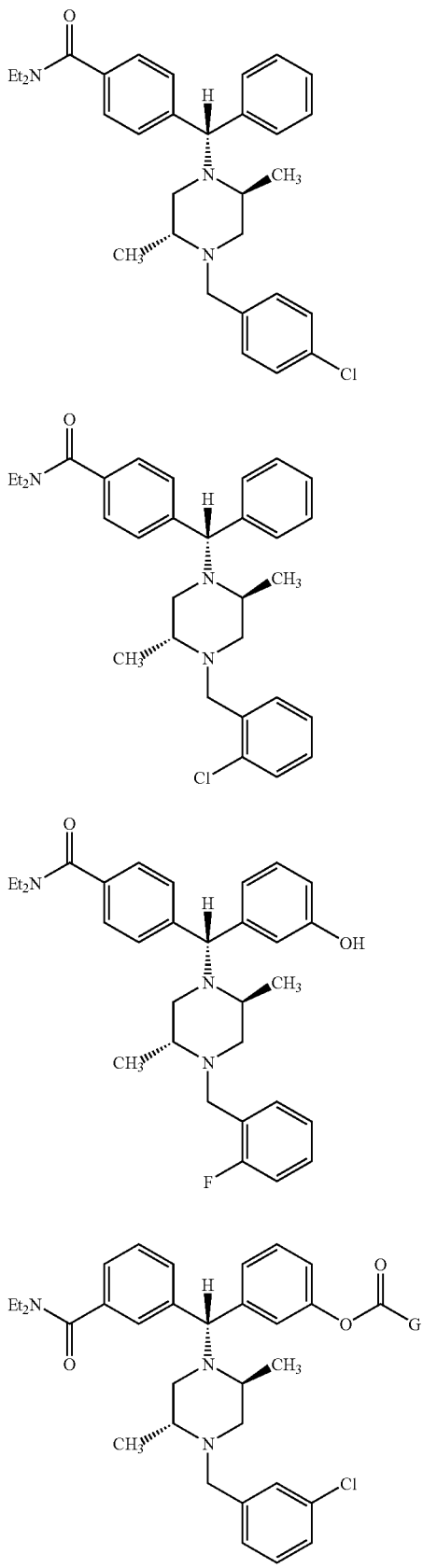

(xviii)

(xix)

(xx)

(xxi)

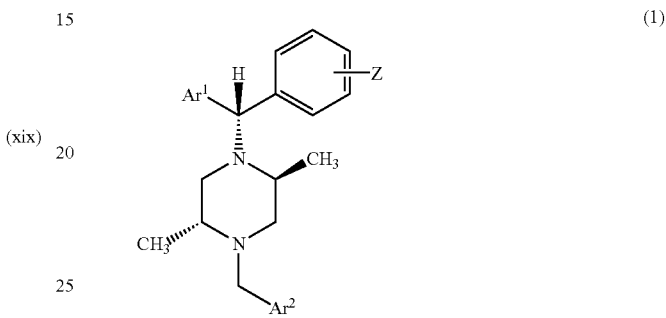

(1)

where G=O-alkyl, N(alkyl)$_2$, and any other pharmaceutically acceptable esters thereof; and pharmaceutically acceptable esters and salts of the foregoing compounds. The therapeutic composition may further include another mood disorder-combating agent including, but not limited to, tricyclic antidepressants, MAO inhibitors, 5-HT agonists and antagonists, aminoketones, serotonin reuptake inhibitors and adrenergic reuptake inhibitors.

Another aspect of the present invention relates to a therapeutic composition for combating a mood disorder in a subject experiencing or susceptible to same, comprising a diarylmethylpiperazine compound of the general formula:

wherein:
Ar$^1$ is a 5- or 6-member carbocyclic or heterocyclic aromatic ring with atoms selected from the group consisting of carbon, nitrogen, oxygen and sulfur, and having on a first carbon atom thereof a substituent Y and on a second ring carbon thereof a substituent R$^1$,
Y is selected from the group consisting of:
hydrogen;
halogen;
C$_1$–C$_6$ alkyl, C$_2$–C$_6$ alkenyl, C$_2$–C$_6$ alkynyl;
C$_1$–C$_6$ haloalkyl;
C$_1$–C$_6$ alkoxy;
C$_3$–C$_6$ cycloalkoxy;
sulfides of the formula SR$^8$ where R$^8$ is C$_1$–C$_6$ alkyl, C$_2$–C$_6$ alkenyl, C$_2$–C$_6$ alkynyl, C$_3$–C$_6$ cycloalkyl, arylalkyl having a C$_5$–C$_{10}$ aryl moiety and an C$_1$–C$_6$ alkyl moiety, or C$_5$–C$_{10}$ aryl;
sulfoxides of the formula SOR$^8$ where R$^8$ is the same as above;
sulfones of the formula SO$_2$R$^8$ where R$^8$ is the same as above;
nitrile;
C$_1$–C$_6$ acyl;
alkoxycarbonylamino (carbamoyl) of the formula NHCO$^2$R$^8$ where R$^8$ is the same as above;
carboxylic acid, or an ester, amide, or salt thereof;
aminomethyl of the formula CH$_2$NR$^9$R$^{10}$ where R$^9$ and R$^{10}$ may be the same or different, and may be hydrogen, C$_1$–C$_6$ alkyl, C$_2$–C$_6$ alkenyl, C$_2$–C$_6$ alkynyl, C$_2$–C$_6$ hydroxyalkyl, C$_2$–C$_6$ methoxyalkyl, C$_3$–C$_6$ cycloalkyl, or C$_5$–C$_{10}$ aryl, or R$^9$ and R$^{10}$ together may form a ring of 5 or 6 atoms, the ring atoms selected from the group consisting of N and C;
carboxamides of the formula CONR$^9$R$^{10}$ where R$^9$ and R$^{10}$ are the same as above, or C$_2$–C$_{30}$ peptide conjugates thereof; and
sulfonamides of the formula SO$_2$NR$^9$R$^{10}$ where R$^9$ and R$^{10}$ are the same as above;

R¹ is hydrogen, halogen, or $C_1$–$C_4$ alkyl, $C_2$–$C_4$ alkenyl, $C_1$–$C_4$ alkynyl;

Z is selected from the group consisting of hydrogen, hydroxyl, halogen and alkoxy;

Ar² is a 5 or 6-member carbocyclic or heterocyclic aromatic ring with atoms selected from the group consisting of carbon, nitrogen, oxygen and sulfur, and having on a carbon atom thereof a substituent X X is selected from the group consisting of hydrogen, halogen (fluorine, bromine, chlorine, iodine), hydroxy and alkoxy;

or a pharmaceutically acceptable ester or salt thereof; and another mood disorder-combating agent, e.g., an additional agent selected from the group consisting of tricyclic antidepressants, MAO inhibitors, 5-HT agonists and antagonists, aminoketones, serotonin reuptake inhibitors, adrenergic reuptake inhibitors, and the like.

Another aspect of the present invention relates to a therapeutic composition for combating a mood disorder in a subject experiencing or susceptible to same, comprising a diarylmethylpiperazine compound of the general formula:

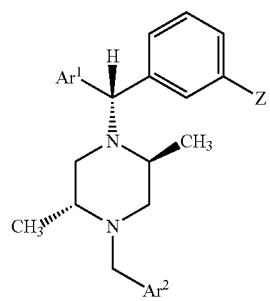

(2)

wherein:

Ar¹ is 6-member carbocyclic aromatic ring having on a carbon atom thereof a substituent Y, wherein Y is a carboxamide of the formula $CONR^9R^{10}$ where $R^9$ and $R^{10}$ are both an ethyl group;

Z is selected from the group consisting of hydrogen, hydroxyl, and alkoxy; and

Ar² is a 6-member carbocyclic aromatic ring having on a carbon atom thereof a substituent X and wherein X is a halogen, or a pharmaceutically acceptable ester or salt thereof.

The therapeutic composition comprising a diarylmethylpiperazine compound of the general formula (2) may be used alone or may be used in combination with another mood disorder-combating agent to combat a mood disorder in a subject experiencing or susceptible to same when administering to said subject an effective amount of the therapeutic composition.

Various other aspects, features and embodiments of the invention will be more fully apparent from the ensuing disclosure and appended claims.

DETAILED DESCRIPTION OF THE INVENTION, AND PREFERRED EMBODIMENTS THEREOF

In one broad method aspect of the present invention, a diarylmethylpiperazine compound as hereinafter more fully described, is administered to a subject in need of treatment of a mood disorder or other pathological emotional condition, for such treatment.

The diarylmethylpiperazine compound may be substituted on the piperazine ring thereof with a benzyl or other arylalkyl or arylcarbyl group, whose aryl moiety is optionally substituted with hydrogen, one or more halo substituents, or an alkoxy group, and such compound or a pharmaceutically acceptable ester or salt of such compound, is administered to a subject in need of treatment. Such compound may be a compound of the aforementioned general formula (1) or (2), including any compounds of the various formulae (i)–(xxi) described hereinabove.

The invention broadly contemplates the treatment of mood disorders and other pathological mental and emotional states, including, without limitation, those involving depression, e.g., bipolar manic-depression, seasonal affective disorder, etc. The treatment in accordance with the invention may advantageously utilize mono-therapy treatment, involving compounds of the invention as singular therapeutic agents in administered therapeutic compositions, or co-therapy treatment, wherein a compound in accordance with the present invention is administered contemporaneously, e.g., simultaneously, or sequentially, with another therapeutic agent. As an illustrative example of such co-therapy treatment, bipolar manic depression is treated by co-therapy involving administration of lithium chloride and a diarylmethylpiperazine compound of the invention.

In a particularly preferred method aspect of the invention, depression is treated by administering to a subject in need of such treatment an effective amount of a compound of formulae (i)–(xxi) or a pharmaceutically acceptable ester or salt thereof.

Examples of pharmaceutically acceptable esters of compounds of formulae (1) and (2) include carboxylic acid esters of the hydroxyl group in the compounds of formula (1) and (2) where Z=OH in which the non-carbonyl moiety of the carboxylic acid portion of the ester grouping is selected from straight or branched chain alkyl (e.g. n-propyl, t-butyl, n-butyl), alkoxyalkyl (e.g. methoxymethyl), arylalkyl (e.g. benzyl), aryloxyalky (e.g. phenoxymethyl), and aryl (e.g. phenyl); alkyl-, aryl-, or arylalkylsulfonyl (e.g. methanesulfonyl); amino acid esters (e.g. L-valyl or L-isoleucyl); dicarboxylic acid esters (e.g. hemisuccinate); carbonate esters (e.g. ethoxycarbonyl); carbamate esters (e.g. dimethylaminocarbonyl, (2-aminoethyl)aminocarbonyl); and inorganic esters (e.g. mono-, di- or triphosphate).

Examples of pharmaceutically acceptable salts of the compounds of formulae (1) and (2) include salts derived from an appropriate base, such as an alkali metal (for example, sodium, potassium), an alkaline earth metal (for example, calcium, magnesium), ammonium and $NR^{\prime 4+}$ (wherein R' is $C_1$–$C_4$ alkyl). Pharmaceutically acceptable salts of an amino group include salts of: organic carboxylic acids such as acetic, lactic, tartaric, malic, lactobionic, fumaric, and succinic acids; organic sulfonic acids such as methanesulfonic, ethanesulfonic, isethionic, benzenesulfonic and p-toluenesulfonic acids; and inorganic acids such as hydrochloric, hydrobromic, sulfuric, phosphoric and sulfamic acids. Pharmaceutically acceptable salts of a compound having a hydroxyl group consist of the anion of said compound in combination with a suitable cation such as $Na^+$, $NH_4^+$, or $NR'_4^+$ (wherein R' is for example a $C_{1-4}$ alkyl group).

For therapeutic use, salts of the compounds of formulae (i)–(xxi) will be pharmaceutically acceptable, i.e., they will be salts derived from a pharmaceutically acceptable acid or base. However, salts of acids or bases that are not pharmaceutically acceptable may also find use, for example, in the preparation or purification of a pharmaceutically acceptable compound. All salts, whether or not derived from a pharmaceutically acceptable acid or base, are within the scope of the present invention.

The delta opioid receptor binding compound employed in the broad practice of the invention may be of any suitable type, e.g., a diarylmethylpiperazine compound optionally substituted on the piperazine ring with a benzyl substituent which in turn is optionally substituted on the phenyl ring of the benzyl group with hydrogen, alkoxy or at least one halogen substituent, or alternatively a diarylmethylpiperazine compound substituted on the piperazine ring with an arylalkyl group whose aryl moiety is a pyridine ring or other heterocyclic moiety.

In one particularly preferred aspect of the invention, the therapeutic treatment agent is a diarylmethylpiperazine compound of formulae (i)–(xxi) or a pharmaceutically acceptable ester or salt thereof.

As used herein, in reference to the present invention, the term "alkyl" is intended to be broadly construed as encompassing: (i) alkyl groups of straight-chain as well as branched chain character; (ii) unsubstituted as well as substituted alkyl groups, wherein the substituents of substituted alkyl groups may include any sterically acceptable substituents which are compatible with such alkyl groups and which do not preclude the efficacy of the diarylmethylpiperazine compound for its intended utility (examples of substituents for substituted alkyl groups include halogen (e.g., fluoro, chloro, bromo, and iodo), amino, amido, $C_1$–$C_4$ alkyl, $C_1$–$C_4$ alkoxy, nitro, hydroxy, etc.); (iii) saturated alkyl groups as well as unsaturated alkyl groups, the latter including groups such as alkenyl-substituted alkyl groups (e.g., allyl, methallyl, propallyl, butenylmethyl, etc.), alkynyl-substituted alkyl groups, and any other alkyl groups containing sterically acceptable unsaturation which is compatible with such alkyl groups and which does not preclude the efficacy of the diarylmethylpiperazine compound for its intended utility; and (iv) alkyl groups including linking or bridge moieties, e.g., heteroatoms such as nitrogen, oxygen, sulfur, etc.

As used herein, in reference to the present invention, the term "aryl" is intended to be broadly construed as referring to carbocyclic (e.g., phenyl, naphthyl) as well as heterocyclic aromatic groups (e.g., pyridyl, thienyl, furanyl, etc.) and encompassing unsubstituted as well as substituted aryl groups, wherein the substituents of substituted aryl groups may include any sterically acceptable substituents which are compatible with such aryl groups and which do not preclude the efficacy of the diarylmethylpiperazine compound for its intended utility. Examples of substituents for substituted aryl groups include hydrogen, one or more of halogen (e.g., fluoro, chloro, bromo, and iodo), amino, amido, $C_1$–$C_4$ alkyl, $C_1$–$C_4$ alkoxy, nitro, trifluoromethyl, hydroxy, hydroxyalkyl containing a $C_1$–$C_4$ alkyl moiety, etc.

The compounds contemplated by the invention include those of the general formulae (1) and (2) per se, as well as physiologically functional derivatives thereof.

By "physiologically functional derivative" is meant a pharmaceutically acceptable salt, ether, ester or salt of an ether or ester of the compound of the general formula (1) or (2) or any other compound which, upon administration to the recipient, is capable of providing (directly or indirectly) the said compound of the general formula (1) or (2) or an active metabolite or residue thereof. Phenolic $C_1$–$C_6$ alkyl ethers are a sub-class of physiologically functional derivatives of the compounds of formulae (i)–(xxi).

The present invention also contemplates pharmaceutical formulations, both for veterinary and for human medical use, which comprise as the active agent one or more compound(s) of the invention.

In such pharmaceutical formulations, the active agent preferably is utilized together with one or more pharmaceutically acceptable carrier(s) therefor and optionally any other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above, and in a quantity appropriate to achieve the desired daily dose.

The formulations include those suitable for parenteral as well as non-parenteral administration, and specific administration modalities include oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

When the active agent is utilized in a formulation comprising a liquid solution, the formulation advantageously may be administered parenterally. When the active agent is employed in a liquid suspension formulation or as a powder in a biocompatible carrier formulation, the formulation may be advantageously administered orally, rectally, or bronchially.

When the active agent is utilized directly in the form of a powdered solid, the active agent may advantageously administered orally. Alternatively, it may be administered bronchially, via nebulization of the powder in a carrier gas, to form a gaseous dispersion of the powder that is inspired by the patient from a breathing circuit comprising a suitable nebulizer device.

In some applications, it may be advantageous to utilize the active agent in a "vectorized" form, such as by encapsulation of the active agent in a liposome or other encapsulant medium, or by fixation of the active agent, e.g., by covalent bonding, chelation, or associative coordination, on a suitable biomolecule, such as those selected from proteins, lipoproteins, glycoproteins, and polysaccharides.

The formulations comprising the active agent of the present invention may conveniently be presented in unit dosage forms and may be prepared by any of the methods well known in the art of pharmacy. Such methods generally include the step of bringing the active compound(s) into association with a carrier that constitutes one or more accessory ingredients. Typically, the formulations are prepared by uniformly and intimately bringing the active compound(s) into association with a liquid carrier, a finely divided solid carrier, or both, and then, if necessary, shaping the product into dosage forms of the desired formulation.

Formulations of the present invention suitable for oral administration may be presented as discrete units such as capsules, cachets, tablets, or lozenges, each containing a predetermined amount of the active ingredient as a powder or granules; or a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Nasal spray formulations comprise purified aqueous solutions of the active compounds with preservative agents and isotonic agents. Such formulations are preferably adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

Transdermal formulations may be prepared by incorporating the active agent in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, formulations of this invention may further include one or more accessory ingredient(s) selected from diluents, buffers, flavoring agents, binders, disintegrants, surface active agents, thickeners, lubricants, preservatives (including antioxidants), and the like.

Depending on the specific condition to be treated, animal subjects may be administered compounds of the present invention at any suitable therapeutically effective and safe dosage, as may readily be determined within the skill of the art, and without undue experimentation.

In general, while the effective dosage of compounds of the invention for therapeutic use may be widely varied in the broad practice of the invention, depending on the specific condition involved, as readily determinable within the skill of the art, suitable therapeutic doses of the compounds of the invention, for each of the appertaining compositions described herein, and for achievement of therapeutic benefit in treatment of each of the conditions described herein, will be in the range of 10 micrograms (µg) to 100 milligrams (mg) per kilogram body weight of the recipient per day, preferably in the range of 50 µg to 75 mg per kilogram body weight per day, and most preferably in the range of 100 µg to 50 mg per kilogram body weight per day. The desired dose is may be presented as two, three, four, five, six, or more sub-doses administered at appropriate intervals throughout the day. These sub-doses may be administered in unit dosage forms, for example, containing from 10 µg to 1000 mg, preferably from 50 µg to 500 mg, more preferably from 50 µg to 250 mg, and most preferably from 50 µg to 10 mg of active ingredient per unit dosage form.

The mode of administration and dosage forms will of course affect the therapeutic amounts of the compounds which are desirable and efficacious for the given treatment application.

For example, orally administered dosages typically are at least twice, e.g., 2–10 times, the dosage levels used in parenteral administration methods, for the same active ingredient. In oral administration, dosage levels for compounds of the present invention may be on the order of 5–200 mg/70 kg body weight/day. In tablet dosage forms, typical active agent dose levels are on the order of 10–100 mg per tablet.

The following examples are illustrative of synthetic procedures that may be advantageously utilized to make compounds of the present invention.

EXAMPLE 1

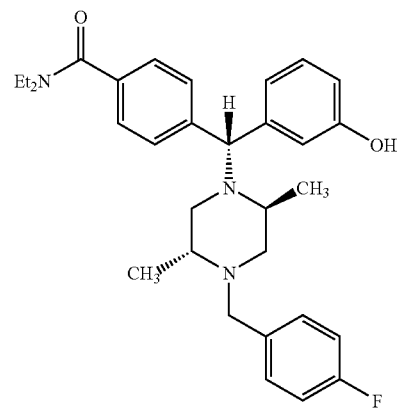

4-((alpha-R)-alpha-((2S,5R)-2,5-Dimethyl-4-(4-fluorobenzyl)-1-piperazinyl)-3-hydroxybenzyl)-N,N-diethylbenzamide A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230–400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture 3-bromophenoxy-tert-butyldimethylsilane (27.3 g, 92.6 mmol) and dibromoethane (3.45 g, 18.4 mmol) in 100 mL of inhibitor-free anhydrous tetrahydrofuran to a solution of magnesium turnings (3.57 g, 147 mmol) in 200 mL of inhibitor-free anhydrous tetrahydrofuran at reflux. After stirring for one hour at reflux the light brown clear mixture was cooled to room temperature.

4-Carboxybenzaldehyde (100.3 g, 0.67 mol) was dissolved/suspended in toluene (1200 mL, dimethylformamide (0.15 mL) added and the suspension stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water 2×300 mL), dilute sodium carbonate solution (saturated:$H_2O$, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil, which was used without further purification. (Yield 115.7 g, 84%)

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Technology, Ltd., Cambridge, England) with 400 mL of toluene. The reaction was heated to reflux under nitrogen until no additional water was observed in the trap (ca. 2 hours). The reaction was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of 20 mL of saturated aqueous ammonium chloride. Anhydrous magnesium sulfate was added and the reaction was filtered. Solvent was removed under vacuum and the residue was redissolved in 800 mL of ethyl acetate. The ethyl acetate solution was washed with 4×200 mL of 1 M sodium hydroxide, 200 mL of water, and 200 mL of saturated aqueous sodium chloride. The organic layer was dried over anhydrous magnesium sulfate and the solvent was removed to give 32.7 g of dark oil. The oil was dissolved in 250 mL of tetrahydrofuran and 250 mL of 3 M hydrochloric acid and stirred for 2 hours at room temperature. The reaction solution was extracted with 3×250 mL of 2:1 diethyl ether/ethyl acetate. Ethyl acetate (300 mL) was added to the aqueous layer and pH was adjusted to 8 with aqueous sodium hydroxide. Layers were separated and the aqueous portion was extracted with another 3×300 mL of ethyl acetate. The combined organic extracts were washed with saturated aqueous sodium chloride, dried over anhydrous sodium sulfate, and the solvent was removed under vacuum to give 12.4 g of brown residue. The residue was purified by chromatography on 300 g of silica gel, eluting with a gradient of 1–15% ethanol in dichloromethane, to give 5.54 g of 4-((alpha-R)-alpha-((2S,5R)-4-allyl-2,5-dimethyl-1-piperazinyl)-3-hydroxybenzyl)-N,N-diethylbenzamide as a colorless gum (27% from 4-formyl-N,N-diethylbenzamide).

4-((alpha-R)-alpha-((2S,5R)-4-Allyl-2,5-dimethyl-1-piperazinyl)-3-hydroxybenzyl)-N,N-diethylbenzamide (0.87 g, 2.0 mmol) was dissolved in methylene chloride (10 mL) and triethylamine (0.919 mL, 0.667 g, 6.6 mmol) was added. N-Phenyl bis(trifluoromethanesulfonimide) (0.785 g, 2.2 mmol) was added and the reaction mixture was sealed under nitrogen and stirred at room temperature overnight. The reaction mixture was evaporated to dryness, the residue dissolved in ethyl acetate (20 mL), and the solution extracted with 5% sodium carbonate solution (2×15 mL). The organic layer was separated, dried over anhydrous sodium sulfate and evaporated to yield a viscous amber oil. The residue was dissolved in methylene chloride (5 mL), applied to a column of silica gel (4×30 cm), and eluted with ethanol/methylene chloride (2:98 v/v). Pure fractions containing desired product, as evidenced by t.l.c. (silica gel, $EM60F_{254}$, 2% $NH_4OH$ in ethyl acetate, $R_f$=0.78) were evaporated to dryness to yield 4-((alpha-R)-alpha-((2S,5R)-4-Allyl-2,5-dimethyl-1-piperazinyl)-3-trifluoromethylsulfonyloxybenzyl)-N,N-diethylbenzamide (0.72 g) as a yellow/amber oil. $^1$H NMR ($CDCl_3$, 500 MHz); δ 1.00 (d, J=6.2 Hz, 3H); 1.12 (br m, 3H); 1.21 (d, J=6.1 Hz, 3H); 1.25 (br m, 3H); 1.83 (t, J=10.6 Hz, 1H); 2.60 (m, 3H); 2.91 (dd J=11.4, 2.7, 1H); 3.02 (m, 1H); 3.18 (br s, 2H); 3.28 (br m, 2H); 3.46 (dd, J=13.7, 5.5 Hz, 1H); 3.55 (br m, 2H); 5.25 (m, 2H); 5.31 (s, 1H); 5.88 (m, 1H); 7.02 (d, J=7.7 Hz, 1H); 7.05 (s, 1H); 7.23 (m, 2H); 7.32 (d, J=8.1 Hz, 2H); 7.40 (d, J=8.1 Hz, 2H); 7.46 (t, J=7.9 Hz, 1H).

A solution of 4-((alpha-R)-alpha-((2S,5R)-4-allyl-2,5-dimethyl-1-piperazinyl)-3-trifluoromethylsulfonyloxybenzyl)-N,N-diethylbenzamide (0.72 g, 1.286 mmol) and thiosalicylic acid (234.7 mg, 1.522 mmol) in anhydrous tetrahydrofuran (4 mL) was stirred under nitrogen for 3 h at room temperature with a catalyst solution prepared by dissolution of bis(dibenzylidineacetone)palladium (36.46 mg, 0.0634 mmol) and 1,4-bis(diphenylphosphino)butane (27.04 mg, 0.0634 mmol) in tetrahydrofuran (0.5 mL). The reaction mixture was evaporated to dryness, the residue dissolved in a mixture of ethyl acetate/ether (1:3, 20 mL) and extracted with 5% sodium carbonate solution (2×15 mL). The organic layer was diluted with two volumes of pentane and extracted with 3M-hydrochloric acid (5×4 mL). The aqueous solution was adjusted to pH 9–10 with concentrated ammonia solution and extracted with methylene chloride (3×10 mL). The combined organic extracts were dried over anhydrous sodium sulfate and evaporated to yield 4-((alpha-R)-alpha-((2S,5R)-2,5-dimethyl-1-piperazinyl)-3-trifluoromethylsulfonyloxybenzyl)-N,N-diethylbenzamide as a brittle pale yellow foam (0.63 g). The product showed a single spot on thin layer chromatography (silica gel, $EM60F_{264}$, 2% $NH_4OH$ in ethyl acetate, $R_f$=0.33). $^1$H NMR ($CDCl_3$, 500 MHz); δ 0.95 (d, J=6 Hz, 3H); 1.13 (br m, 3H); 1.20 (d, J=6.1 Hz, 3H); 1.26 (br m, 3H); 1.50 (t, J=9.7 Hz, 1H); 2.31 (m, 1H); 2.64 (dd J=11.3, 2.5, 1H); 2.71 (m, 1H); 2.95 (m, 1H); 3.29 (br m, 2H); 3.56 (br m, 2H); 5.43 (s, 1H); 7.04 (m, 1H); 7.21 (d, J=7.7, 1H); 7.24 ( dd, J=8.2, 2.2 Hz, 1H); 7.34 (d, J=8.2 Hz, 2H); 7.42 (d, J=8.1 Hz, 2H); 7.48 (t, J=8 Hz, 1H).

4-((alpha-R)-alpha-((2S,5R)-2,5-Dimethyl-1-piperazinyl)-3-trifluoromethylsulfonyloxybenzyl)-N,N-diethylbenzamide (527.6 mg, 1.0 mmol) was dissolved in acetonitrile (4.0 mL) and sodium iodide (30 mg, 0.2 mmol) added. The suspension was stirred during the addition of triethylamine (800 μL (580.8 mg), 5.74 mmol), followed by 4-fluorobenzyl bromide (249 μL, 378 mg, 2.0 mmol). The reaction mixture was sealed under nitrogen and stirred overnight at room temperature. The reaction mixture was evaporated to dryness and the residue dissolved in ethyl acetate (10 mL). The organic solution was washed with saturated aqueous sodium bicarbonate solution (2×5 mL) and saturated sodium chloride solution (5 mL), dried over anhydrous sodium sulfate, and evaporated to a golden oil (a single spot on silica gel, EM60F$_{264}$, 2% NH$_4$OH in ethyl acetate, R$_f$=0.86). This intermediate 4-((alpha-R)-alpha-((2S,5R)-2,5-Dimethyl-4-(4-fluorobenzyl)-1-piperazinyl)-3-trifluoromethylsulfonyloxybenzyl)-N,N-diethylbenzamide (608.9 mg) was used without further purification. The oil was dissolved in ethanol (8 mL) and aqueous 2.5 M (10%) sodium hydroxide solution (5 mL, 12.5 mmol) was added. The reaction mixture was stirred at room temperature for 3.5 h, then the ethanol was removed by evaporation. The oily suspension of the sodium salt was clarified by the addition of water (7.5 mL), and the pH of the solution adjusted to 8.5–9 by the passage of gaseous carbon dioxide (from dry ice). The copious white precipitate was collected by filtration, washed well with water, and dried under vacuum (2 mm Hg) at room temperature overnight to yield 4-((alpha-R)-alpha-((2S,5R)-2,5-dimethyl-4-(4-fluorobenzyl)-1-piperazinyl)-3-hydroxybenzyl)-N,N-diethylbenzamide as a white solid (423.6 mg, 84%). Calc. for C$_{31}$H$_{38}$FN$_3$O$_2$ C, 73.93; H, 7.61; N, 8.34. Found C, 73.91; H, 7.65; N, 8.21%. $^1$H NMR (CDCl$_3$, 300 MHz); δ 1.05 (d, J=6.3 Hz, 3H); 1.07 (d, J=6.3 Hz, 3H); 1.11 (br m, 3H); 1.25 (br m, 3H); 1.97 (m, 2H); 2.53 (br m, 1H); 2.57 (br m, 1H); 2.61 (dd, J=9, 2.6 Hz, 1H); 2.65 (dd, J=9, 2.4 Hz, 1H); 3.14 (d, J=13 Hz, 1H); 3.28 (br m, 2H); 3.54 (br m, 2H); 3.87 (d, J=13 Hz, 1H); 5.13 (s, 1H); 6.62 (s, 1H); 6.70 (m, 2H); 6.96 (t, J=8.5 Hz, 2H); 7.13 (t, J=7.8 Hz, 1H); 7.24 (m, 2H); 7.28 (d, J=8.2 Hz, 2H); 7,43 (d, J=8.1 Hz, 2H).

EXAMPLE 2

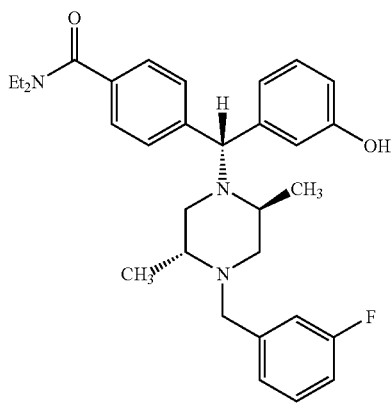

4-((alpha-R)-alpha-((2S,5R)-2,5-Dimethyl-4-(3-fluorobenzyl)-1-piperazinyl)-3-hydroxybenzyl)-N,N-diethylbenzamide A solution of 3-bromophenol (400 g, 2.31 mol), tert-butylchlorodimethylsilane (391 g, 2.54 mol), and imidazole (346 g, 5.08 mol) in 5000 mL of dichloromethane was stirred overnight at room temperature. The reaction solution was poured into 2000 mL of water and the layers were separated. The organic layer was washed with 1N aqueous sodium hydroxide solution (3×1500 mL) and water (2×1500 mL) before passing through a pad of silica gel (400 g, silica 60, 230–400 mesh). The silica gel was washed with dichloromethane (2×500 mL), the filtrates were combined and the solvent removed under reduced pressure to give 669 g (98.4%) of 3-(bromophenoxy)-tert-butyldimethylsilane as a clear pale yellow liquid. NMR (300 MHz, CDCl$_3$): δ 0.2 (s, 6H); 1.0 (s, 9H); 6.75 (m, 1H); 7.0 (br s, 1H); 7.1 (m, 2H).

3-tert-Butyldimethylsilyloxyphenylmagnesium bromide was formed by the slow addition of a mixture 3-bromophenoxy-tert-butyldimethylsilane (27.3 g, 92.6 mmol) and dibromoethane (3.45 g, 18.4 mmol) in 100 mL of inhibitor-free anhydrous tetrahydrofuran to a solution of magnesium turnings (3.57 g, 147 mmol) in 200 mL of inhibitor-free anhydrous tetrahydrofuran at reflux. After stirring for one hour at reflux the light brown clear mixture was cooled to room temperature.

4-Carboxybenzaldehyde (100.3 g, 0.67 mol) was dissolved/suspended in toluene (1200 mL, dimethylformamide (0.15 mL) added and the suspension stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water 2×300 mL), dilute sodium carbonate solution (saturated:H$_2$O, 1:1, 2×600 mL), water (2×300 mL) and saturated sodium chloride solution (300 mL). The organic layer was separated, dried over anhydrous sodium sulfate and evaporated to yield 4-formyl-N,N-diethylbenzamide as a pale brown oil, which was used without further purification. (Yield 115.7 g, 84%)

In a 1000 mL round bottom flask fitted with a condenser and Dean-Stark trap were combined 4-formyl-N,N-diethylbenzamide (9.50 g, 46.3 mmol), benzotriazole (5.51 g, 46.3 mmol), and (2R,5S)-1-allyl-2,5-dimethylpiperazine (7.15 g, 46.3 mmol, Chirotech Technology, Ltd., Cambridge, England) with 400 mL of toluene. The reaction was heated to reflux under nitrogen until no additional water was observed in the trap (ca. 2 hours). The reaction was cooled to room temperature and concentrated under vacuum to leave a volume of approximately 50 mL. Anhydrous tetrahydrofuran (100 mL) was added to the flask under nitrogen with stirring to dissolve all residue. The solution of benzotriazole adduct was added to the solution of 3-tert-butyldimethylsilyloxyphenylmagnesium bromide (above) at room temperature via double-ended needle. After stirring for 2 hours, the reaction was quenched by addition of 20 mL of saturated aqueous ammonium chloride. Anhydrous magnesium sulfate was added and the reaction was filtered. Solvent was removed under vacuum and the residue was redissolved in 800 mL of ethyl acetate. The ethyl acetate solution was washed with 4×200 mL of 1 M sodium hydroxide, 200 mL of water, and 200 mL of saturated aqueous sodium chloride. The organic layer was dried over anhydrous magnesium sulfate and the solvent was removed to give 32.7 g of dark oil. The oil was dissolved in 250 mL of tetrahydrofuran and 250 mL of 3 M hydrochloric acid and stirred for 2 hours at room temperature. The reaction solution was extracted with 3×250 mL of 2:1 diethyl ether/ethyl acetate. Ethyl acetate (300 mL) was added to the aqueous layer and pH was adjusted to 8 with aqueous sodium hydroxide. Layers were separated and the aqueous portion was extracted with another 3×300 mL of ethyl acetate. The combined organic extracts were washed with saturated aqueous sodium chloride, dried over anhydrous sodium sulfate, and the solvent was removed under vacuum to give 12.4 g of brown residue. The residue was purified by chromatography on 300 g of silica gel, eluting with a gradient of 1–15% ethanol in dichloromethane, to give 5.54 g of 4-((alpha-R)-alpha-((2S, 5R)-4-allyl-2,5-dimethyl-1-piperazinyl)-3-hydroxybenzyl)-N,N-diethylbenzamide as a colorless gum (27% from 4-formyl-N,N-diethylbenzamide).

4-((alpha-R)-alpha-((2S,5R)-4-Allyl-2,5-dimethyl-1-piperazinyl)-3-hydroxybenzyl)-N,N-diethylbenzamide (4.87 g, 11.2 mmol) was dissolved in methylene chloride (60 mL) and triethylamine (5.15 mL, 3.73 g, 37 mmol) was added. N-Phenyl bis(trifluoromethanesulfonimide) (4.40 g, 12.3 mmol) was added and the reaction mixture was sealed under nitrogen and stirred at room temperature overnight. The reaction mixture was evaporated to dryness, the residue dissolved in ethyl acetate (100 mL), and the solution extracted with 5% sodium carbonate solution (2×75 mL). The organic layer was separated, dried over anhydrous sodium sulfate and evaporated to yield a viscous amber oil. The residue was dissolved in methylene chloride (30 mL), applied to a column of silica gel (1000 g), and eluted with ethanol/methylene chloride (2:98 v/v).

Pure fractions containing desired product, as evidenced by t.l.c. (silica gel, EM60F$_{254}$, 2% NH$_4$OH in ethyl acetate, R$_f$=0.78) were evaporated to dryness to yield 4-((alpha-R)-alpha-((2S,5R)-4-Allyl-2,5-dimethyl-1-piperazinyl)-3-trifluoromethylsulfonyloxybenzyl)-N,N-diethylbenzamide (4.03 g) as a yellow/amber oil. $^1$H NMR (CDCl$_3$, 500 MHz); δ 1.00 (d, J=6.2 Hz, 3H); 1.12 (br m, 3H); 1.21 (d, J=6.1 Hz, 3H); 1.25 (br m, 3H); 1.83 (t, J=10.6 Hz, 1H); 2.60 (m, 3H); 2.91 (dd J=11.4, 2.7, 1H); 3.02 (m, 1H); 3.18 (br s, 2H); 3.28 (br m, 2H); 3.46 (dd, J=13.7, 5.5 Hz, 1H); 3.55 (br m, 2H); 5.25 (m, 2H); 5.31 (s, 1H); 5.88 (m, 1H); 7.02 (d, J=7.7 Hz, 1H); 7.05 (s, 1H); 7.23 (m, 2H); 7.32 (d, J=8.1 Hz, 2H); 7.40 (d, J=8.1 Hz, 2H); 7.46 (t, J=7.9 Hz, 1H).

A solution of 4-((alpha-R)-alpha-((2S,5R)-4-allyl-2,5-dimethyl-1-piperazinyl)-3-trifluoromethylsulfonyloxybenzyl)-N,N-diethylbenzamide (4.03 g, 7.20 mmol) and thiosalicylic acid (1.32 g, 8.52 mmol) in anhydrous tetrahydrofuran (25 mL) was stirred under nitrogen for 3 h at room temperature with a catalyst solution prepared by dissolution of bis(dibenzylidineacetone)palladium (204 mg, 0.355 mmol) and 1,4-bis(diphenylphosphino)butane (151 mg, 0.355 mmol) in tetrahydrofuran (3 mL). The reaction mixture was evaporated to dryness, the residue dissolved in a mixture of ethyl acetate/ether (1:3, 125 mL) and extracted with 5% sodium carbonate solution (2×75 mL). The organic layer was diluted with two volumes of pentane and extracted with 3M-hydrochloric acid (5×25 mL). The aqueous solution was adjusted to pH 9–10 with concentrated ammonia solution and extracted with methylene chloride (3×50 mL). The combined organic extracts were dried over anhydrous sodium sulfate and evaporated to yield 4-((alpha-R)-alpha-((2S,5R)-2,5-dimethyl-1-piperazinyl)-3-trifluoromethylsulfonyloxybenzyl)-N,N-diethylbenzamide as a brittle pale yellow foam (3.53 g). The product showed a single spot on thin layer chromatography (silica gel, EM60F$_{264}$, 2% NH$_4$OH in ethyl acetate, R$_f$=0.33). $^1$H NMR (CDCl$_3$, 500 MHz); δ 0.95 (d, J=6 Hz, 3H); 1.13 (br m, 3H); 1.20 (d, J=6.1 Hz, 3H); 1.26 (br m, 3H); 1.50 (t, J=9.7 Hz, 1H); 2.31 (m, 1H); 2.64 (dd J=11.3, 2.5, 1H); 2.71 (m, 1H); 2.95 (m, 1H); 3.29 (br m, 2H); 3.56 (br m, 2H); 5.43 (s, 1H); 7.04 (m, 1H); 7.21 (d, J=7.7, 1H); 7.24 (dd, J=8.2, 2.2 Hz, 1H); 7.34 (d, J=8.2 Hz, 2H); 7.42 (d, J=8.1 Hz, 2H); 7.48 (t, J=8 Hz, 1H).

A solution of 4-((alpha-R)-alpha-((2S,5R)-2,5-dimethyl-1-piperazinyl)-3-trifluoromethylsulfonyloxybenzyl)-N,N-diethylbenzamide (3.522 g, 6.0 mmol) and sodium iodide (90 mg, 0.6 mmol) in acetonitrile (30 mL) was stirred during the addition of triethylamine (3.0 mL, 2.186 g, 21.6 mmol) followed by 3-fluorobenzyl bromide (1.472 mL, 2.268 g, 12.0 mmol). An immediate turbidity was observed, thickening to a white crystalline precipitate as the reaction progressed. The reaction mixture was sealed under nitrogen and stirred at room temperature. After 18 h the solvent was removed by evaporation under reduced pressure and the residue partitioned between ethyl acetate (30 mL) and saturated sodium bicarbonate solution (10 mL). The organic layer was separated and the aqueous portion further extracted with ethyl acetate (3×15 mL). The combined extract and washings were dried over sodium sulfate, the solution evaporated to dryness and re-dissolved in ethyl acetate (~5 mL). The solution was applied to an intermediate (4×15 cm) Biotage column and eluted with ethyl acetate, collecting fractions of 20 mL. Fractions containing pure material as evidenced by thin layer chromatography (silica, EM60F$_{254}$, developed with ethyl acetate, R$_f$ 0.9) were pooled and evaporated to yield a yellow/orange oil (3.01 g). The oil was dissolved in ethanol (30 mL) and aqueous sodium hydroxide solution (10.0 mL, 2.5-M, 25 mmol) was added. The initially cloudy suspension clarified to a yellow solution that was set aside at room temperature for 3 h. The mixture was evaporated under reduced pressure to remove ethanol, and evaporation continued until condensation of water indicated complete removal of ethanol. The cloudy suspension of the oily sodium salt of the phenol was diluted to 20 mL with water to yield a clear yellow solution. The pH of the strongly basic solution was adjusted to 8.5–9 by passage of carbon dioxide gas (from dry ice) to yield a dense white flocculent precipitate. The solid was removed by filtration and washed thoroughly with cold water, including twice re-slurrying of the precipitate on the sinter with fresh water. The solid was air-dried on the sinter overnight, then dried under vacuum at 1 mm Hg at room temperature to yield 4-((alpha-R)-alpha-((2S,5R)-2,5-dimethyl-4-(3-fluorobenzyl)-1-piperazinyl)-3-hydroxybenzyl)-N,N-diethylbenzamide as a white solid (2.062 g, 67%) Calc. for C$_{31}$H$_{38}$FN$_3$O$_2$ 0.5 H$_2$O: C, 72.63; H, 7.67; N, 8.20; F, 3.71. Found C, 72.77; H, 7.52; N, 8.18; F, 3.61%. $^1$H NMR (CDCl3, 300 MHz); δ 1.05 (d, J=5.9 Hz, 6H); 1.11 (br m, 3H); 1.23 (br m, 3H); 2.00 (m, 2H); 2.59 (br m, 2H); 2.62 (d, J=11.4 Hz, 1H); 2.68 (d, J=11.0 Hz, 1H); 3.19 (d, J=13.6 Hz, 1H); 3.28 (br m, 2H); 3.54 (br m, 2H); 3.89 (d, J=13.9 Hz, 1H); 5.01 (s, 1H); 6.15 (v br s, 1H); 6.63 (s, 1H); 6.70 (m, 2H); 6.91 (t, J=8.8 Hz, 1H); 7.07 (m, 2H); 7.14 (t, J=7.8 Hz, 1H); 7.22 (m, 1H); 7.28 (d, J=8.2 Hz, 2H); 7.44 (d, J=8.1 Hz, 2H).

The following compounds were prepared from 4-((alpha-R)-alpha-((2S,5R)-2,5-dimethyl-1-piperazinyl)-3-trifluoromethylsulfonyloxy-benzyl)-N,N-diethylbenzamide (intermediate in Example 1) by a similar procedure.

EXAMPLE 3

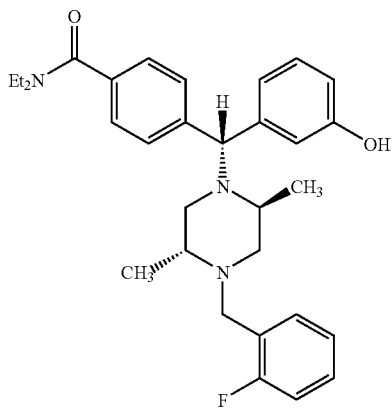

4-((Alpha-R)-Alpha-((2S,5R)-2,5-Dimethyl-4-(2-fluorobenzyl)-1-piperazinyl)-3-hydroxybenzyl)-N,N-diethylbenzamide 4-((alpha-R)-alpha-((2S,5R)-2,5-Dimethyl-1-piperazinyl)-3-trifluoromethylsulfonyloxy-benzyl)-N,N-diethylbenzamide (from Example 1, 527.6 mg, 1.0 mmol) was dissolved in acetonitrile (4.0 mL) and sodium iodide (15 mg, 0.1 mmol) added. The suspension was stirred during the addition of triethylamine (500 µL (363 mg), 3.59 mmol), followed by 2-fluorobenzyl bromide (241 µL (378 mg), 2.0 mmol). The reaction mixture was sealed under nitrogen and stirred overnight at room temperature. The reaction mixture was evaporated to dryness and partitioned between ethyl acetate (10 mL) and saturated aqueous sodium bicarbonate solution (2.5 mL). The supernatant organic layer was removed, and the aqueous portion washed with ethyl acetate (3×10 mL). The combined organic extract and washings were dried over anhydrous sodium sulfate and evaporated to a golden oil. The residue was dissolved in ethyl acetate (7 mL), applied to a pre-packed (Biotage) column and eluted with ethyl acetate. Pure fractions containing desired product, as evidenced by t.l.c. (silica gel, EM60F$_{264}$, 100% ethyl acetate, $R_f$=0.77) were evaporated to dryness to yield the intermediate 4-((alpha-R)-alpha-((2S,5R)-2,5-Dimethyl-4-(2-fluorobenzyl)-1-piperazinyl)-3-trifluoromethylsulfonyloxybenzyl)-N,N-diethylbenzamide (610 mg), as a yellow oil, which was used without further purification. The oil was dissolved in ethanol (7 mL) and aqueous 2.5 M (10%) sodium hydroxide solution (5 mL, 12.5 mmol) was added. The reaction mixture was set aside at room temperature for 5 h, then the ethanol removed by evaporation. The oily suspension of the sodium salt was clarified by the addition of water (5 mL), and the pH of the solution adjusted to 9–10 by the passage of gaseous carbon dioxide (from dry ice). The copious white precipitate was washed well with water and dried under vacuum (2 mm Hg) at room temperature overnight to yield the title compound as a white solid (431 mg, 85.6%). Calc. for $C_{31}H_{38}FN_3O_2$: C, 73.93; H, 7.61; N, 8.34; F, 3.77. Found C, 73.96; H, 7.67; N, 8.29; F, 3.75%. $^1$H NMR (CDCl3, 300 MHz); δ 1.05 (d, J=6.1 Hz, 3H); 1.09 (d, J=6 Hz, 3H); 1.12 (br m, 3H); 1.24 (br m, 3H); 1.96 (t, J=10 Hz, 1H); 2.07 (t, J=10 Hz, 1H); 2.56 (br m, 2H); 2.60 (d, J=11 Hz, 1H); 2.72 (d, J=11 Hz, 1H); 3.29 (br m, 2H); 3.36 (d, J=14 Hz, 1H); 3.55 (br m, 2H); 3.89 (d, J=14 Hz, 1H); 5.13 (s, 1H); 6.57 (s, 1H); 6.66 (d, J=10 Hz, 2H); 7.00 (t, J=9 Hz, 1H); 7.07 (t, J=7.5 Hz, 1H); 7.10 (t, J=8 Hz, 1H); 7.20 (m, 1H); 7.27 (d, J=8 Hz, 2H); 7.38 (t, J=7 Hz, 1H); 7,43 (d, J=7 Hz, 2H).

EXAMPLE 4

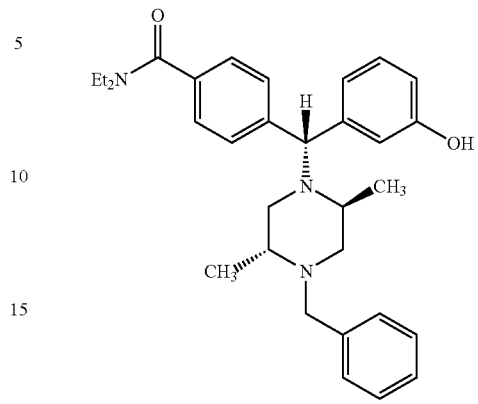

4-((alpha-R)-alpha-((2S,5R)-4-Benzyl-2,5-dimethyl-1-piperazinyl)-3-hydroxybenzyl)-N,N-diethylbenzamide (Yield 88.5%). Calc. for $C_{31}H_{39}N_3O_2$ 0.9 $H_2O$: C, 74.19; H, 8.19; N, 8.37. Found C, 74.20; H, 7.88; N, 8.25%. $^1$H NMR (CDCl3, 300 MHz); δ 1.03 (d, J=6.1 Hz, 3H); 1.09 (d, J=6.1 Hz, 3H); 1.12 (br m, 3H); 1.24 (br m, 3H); 1.99 (m, 2H); 2.53 (br m, 2H); 2.60 (dd, J=9, 2 Hz, 1H); 2.65 (dd, J=9, 2 Hz, 1H); 3.17 (d, J=13 Hz, 1H); 3.29 (br m, 2H); 3.55 (br m, 2H); 3.95 (d, J=13 Hz, 1H); 5.13 (s, 1H); 6.55 (s, 1H); 6.64 (m, 2H); 7.10 (t, J=7.7 Hz, 2H); 7.13 (m, 1H); 7.24 (m, 5H); 7,45 (d, J=8.1 Hz, 2H).

EXAMPLE 5

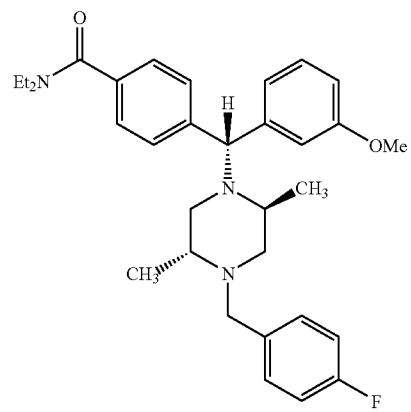

4-((alpha-R)-alpha-((2S,5R)-2,5-Dimethyl-4-(4-fluorobenzyl)-1-piperazinyl)-3-methoxybenzyl)-N,N-diethylbenzamide Sodium hydride (60% dispersion in oil, 400 mg (240 mg NaH, 10 mmol)) was washed with pentane (2×7 mL), then tetrahydrofuran (10 mL) added as supernatant. 4-((alpha-R)-alpha-((2S,5R)-2,5-dimethyl-4-(4-fluorobenzyl)-1-piperazinyl)-3-hydroxybenzyl)-N,N-diethylbenzamide (Example 1, 1.007 g, 2.0 mmol) was dissolved in the stirred suspension, and when effervescence had subsided, methyl iodide (249 µL, 568 mg, 4 mmol) was added. The reaction mixture was sealed under nitrogen and stirred for 6 h at ambient temperature. The reaction mixture was evaporated to dryness, and the residue partitioned between ethyl acetate (15 mL) and water (5 mL). The organic layer was separated, the aqueous portion extracted with ethyl acetate (2×10 mL) and the combined organic extracts dried over anhydrous sodium sulfate. The organic solution was evaporated to a pale yellow gum, which on trituration and sonication with pentane yielded 4-((alpha-R)-alpha-((2S,5R)-2,5-dimethyl-4-(4-fluorobenzyl)-1-piperazinyl)-3-methoxybenzyl)-N,N-diethylbenzamide as a flocculent white solid (0.798 g, 77% after drying at room temperature and 5 mm Hg). Calc. for $C_{32}H_{40}FN_3O_2$ 0.25 $H_2O$: C, 73.60; H, 7.82; N, 8.05; F, 3.64. Found C, 73.58; H, 7.70; N, 8.04; F, 3.84%. $^1$H NMR (CDCl3, 300 MHz); δ 1.09 (d, J=6.2 Hz, 6H, superimposed on br m, 3H); 1.21 (br m, 3H); 1.99 (m, 2H); 2.57 (br m, 2H); 2.66 (m, 3H); 3.15 (d, J=13.3 Hz, 1H); 3.27 (br m, 2H); 3.54 (br m, 2H); 3.78 (s, 3H); 3.84 (d, J=13 Hz, 1H); 5.10 (s, 1H); 6.76 (s, 1H); 6.70 (d, J=8.1 Hz, 2H); 6.96 (t, J=8.2 Hz, 2H); 7.26 (m, 5H); 7.46 (d, J=7.8 Hz, 2H).

EXAMPLE 6

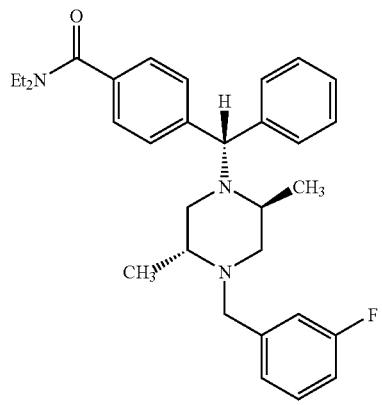

4-((alpha-S)-alpha-((2S,5R)-2,5-Dimethyl-4-(3-fluorobenzyl)-1-piperazinyl)benzyl)-N,N-diethylbenzamide Method 1 a) 4-Formyl-N,N-diethylbenzamide

4-Carboxybenzaldehyde (100.3 g, 0.67 mol) was dissolved/suspended in toluene (1200 mL, dimethylformamide (0.15 mL) added and the suspension stirred during the dropwise addition of thionyl chloride (53.5 mL, 87.2 g, 0.73 mol). The reaction mixture was heated to reflux under nitrogen and stirred for 2 h, during which time much, but not all of the aldehydo-acid passed into solution. A further quantity of thionyl chloride (20 mL, 32.6 g, 0.27 mol) was added and reflux continued overnight. The clear reaction mixture was evaporated, and the residue dissolved in anhydrous tetrahydrofuran (1500 mL). The solution was cooled in an ice/water bath and diethylamine (173 mL, 122 g, 1.67 mol (2.5 equivalents)) was added dropwise to the stirred solution. The ice-bath was removed and stirring continued for 2.5 h. The reaction mixture was filtered to remove the white crystalline diethylamine hydrochloride by-product. The crystals were washed with ethyl acetate (2×600 mL), and the washings set aside. The tetrahydrofuran filtrate was evaporated, and the residue dissolved in the ethyl acetate washings. The solution was washed sequentially with 1 M-hydrochloric acid (2×600 mL), water 2×300 mL), dilute sodium carbonate solution (saturated:$H_2O$, 1:1, 2×600 mL), water (2×300 mL) and saturated sodium chloride solution (300 mL). The organic layer was separated, dried over anhydrous sodium sulfate, and evaporated to yield 4-formyl-N,N-diethylbenzamide as a pale brown oil, which was used without further purification. (Yield 115.7 g, 84%)

b) 4-((alpha-S)-alpha-((2S,5R)-4-Allyl-2,5-dimethyl-1-piperazinyl)benzyl)-N,N-diethylbenzamide A solution of 4-formyl-N,N-diethylbenzamide (51.3 g, 250 mmol), benzotriazole (29.8 g, 250 mmol) and (2R,5S)-1-allyl-2,5-dimethylpiperazine (38.6 g, 250 mmol, Chirotech Technology, Ltd., Cambridge, England) in toluene (2500 mL) was heated under reflux under nitrogen with azeotropic removal of water for 2.5 h. Toluene was removed gradually via the Dean/Stark trap during this period until the residual volume of the reaction mixture was reduced to approximately 700–800 mL. The solution was diluted with anhydrous tetrahydrofuran (1000 mL), cooled to ~0° C. in an ice/isopropanol bath, and stirred under nitrogen during the addition over ~20 min of phenylmagnesium bromide (1.0 M in tetrahydrofuran, 500 mL, 500 mmol) through a wide-bore double-tipped needle. During the addition a suspension of magnesium salts began to form almost immediately, but did not become sufficiently thick to preclude efficient stirring. Initially the suspension was a yellow ochre in color, which persisted until about two-thirds of the Grignard reagent had been added, when the color of the reaction mixture changed rapidly to a ruddy brown. The ice bath was removed and the suspension stirred at ambient temperature for 1.5 h, then quenched with saturated aqueous ammonium chloride solution (125 mL). The yellow suspension was stirred for 30 min, then anhydrous magnesium chloride (125 g) added. The suspension was stirred for a further hour and filtered. The filter cake was washed with tetrahydrofuran (400 mL), and the combined filtrate and washings evaporated to a thick brown oil. The residue was partitioned between ethyl acetate (2500 mL) and aqueous sodium hydroxide solution (1.0 M, 1000 mL). The organic layer was separated and washed successively with 1M-NaOH (3×1000 mL), water (3×1200 mL) and saturated aqueous sodium chloride solution (750 mL). Ethyl acetate (75 mL) was added to the partially crystallizing suspension, yielding a thick slurry of light-colored crystals in a dark mother liquor. The suspension was filtered, and the solid washed sparingly with cold ethyl acetate and dried under vacuum at room temperature to yield a slightly off-white solid (38.31 g). The dark filtrate and washings were evaporated to a dark oil, which again partially crystallized on standing. The residue was triturated with ethyl acetate (20 mL) and filtered to yield a second crop of pale yellow crystals (4.04 g). Total yield of 4-((alpha-S)-alpha-((2S,5R)-4-allyl-2,5-dimethyl-1-piperazinyl)benzyl)-N,N-diethylbenzamide was 42.35 g, (40.4%)

c) 4-((alpha-S)-alpha-((2S,5R)-2,5-Dimethyl-1-piperazinyl)benzyl)-N,N-diethylbenzamide A solution of bis(dibenzylidineacetone)palladium (1.438 g, 2.5 mmol) and 1,4-bis(diphenylphosphino)butane (1.066 g, 2.5 mmol) in tetrahydrofuran (20 mL) was stirred under nitrogen at room temperature for 15 min, then added via syringe to a stirred solution under nitrogen of 4-((alpha-S)-alpha-((2S,5R)-4-allyl-2,5-dimethyl-1-piperazinyl)benzyl)-N,N-diethylbenzamide (20.98 g, 50 mmol) and thiosalicylic acid (9.25 g, 60 mmol) in anhydrous tetrahydrofuran (100 mL). The reaction mixture was stirred under nitrogen for 2 h at room temperature, then evaporated to dryness, the residue dissolved ethyl acetate (120 mL) and diluted with ether (300 mL). The solution was washed with dilute sodium carbonate solution (saturated:H$_2$O, 1:3, 3×200 mL). The organic solution was diluted with pentane (800 mL) and extracted with 3M-hydrochloric acid (5×40 mL), followed by M-hydrochloric acid (3×50 mL, alternating with water (3×50 mL)). The combined aqueous extracts were filtered to remove a small amount of suspended solid and the pH adjusted to 12 with 5-M NaOH. The resulting oily suspension was extracted with methylene chloride (3×150 mL), the combined organic extracts dried over anhydrous sodium sulfate and evaporated to dryness to yield 4-((alpha-S)-alpha-((2S,5R)-2,5-dimethyl-1-piperazinyl)benzyl)-N,N-diethylbenzamide as a very pale yellow solid (18.07 g, 97.8%). The product showed a single spot on thin layer chromatography (silica gel, EM60F$_{264}$, 4% NH$_4$OH/10% EtOH in ethyl acetate, R$_f$=0.25). and was used without further purification. Calc. for C$_{24}$H$_{33}$N$_3$O 0.2 H$_2$O: C, 75.24; H, 8.79; N, 10.97. Found C, 75.24; H, 8.87; N, 10.86%.

d) 4-((alpha-S)-alpha-((2S,5R)-2,5-Dimethyl-4-(3-fluorobenzyl)-1-piperazinyl)benzyl)-N,N-diethylbenzamide A solution of 4-((alpha-S)-alpha-((2S,5R)-2,5-dimethyl-1-piperazinyl)benzyl)-N,N-diethylbenzamide (9.128 g, 24.05 mmol) in acetonitrile (150 mL)) was added to sodium iodide (360 mg, 2.4 mmol) and stirred under nitrogen during the addition of triethylamine (12 mL, (8.76 g), 86.6 mmol), followed by 3-fluorobenzyl bromide (5.9 mL, (9.09 g), 48.1 mmol). An immediate turbidity was observed on addition of the fluorobenzyl bromide, thickening to a white crystalline precipitate over one hour. The reaction mixture was stirred under nitrogen overnight at room temperature. The solvent was removed by evaporation, and saturated sodium bicarbonate solution (25 mL) added to the residue. The copious white precipitate was filtered off, washed well with water and dried under vacuum at room temperature to give 4-((alpha-S)-alpha-((2S,5R)-2,5-dimethyl-4-(3-fluorobenzyl)-1-piperazinyl)benzyl)-N,N-diethylbenzamide (10.54 g, 89.2%). Calc. for C$_{31}$H$_{38}$FN$_3$O 0.2 H$_2$O: C, 75.79; H, 7.88; N, 8.55; F, 3.87. Found C, 75.80; H, 7.78; N, 8.49; F, 3.75%.

Method 2 a) 4-Formyl-N,N-diethylbenzamide

To a 12 L flask equipped with mechanical stirrer and cold bath was charged 300 g (2 mol) of 4-carboxybenzaldehyde, 4.5 L of tetrahydrofuran and 245 g (2.4 mol) of triethylamine. This solution was cooled to −4° C. with methanol/ice bath. To the reaction was charged 236 g (1.9 mol) of pivaloyl chloride at a rate that maintained the temperature below 5° C. After stirring for 2 h the resulting slurry was filtered and the filter cake was washed with 1 L of THF. The filtrates were returned to the reactor and cooled below −5° C. Diethylamine (438 g, 6 mol) was slowly added maintaining the temperature below 0° C. The reaction was stirred for several hours and allowed to warm. The solvent was then removed under vacuum and the resulting residue was dissolved in 2 L of ethyl acetate. The resulting solution was washed with 1 L of water and the aqueous layer was back-extracted with 2×500 mL ethyl acetate. The combined organic layer was washed with 3×500 mL of 1 N HCl and 3×500 mL of NaHCO$_3$ (aq, sat). This solution was dried with Na$_2$SO$_4$ and the solvent was removed under vacuum to give a golden brown oil (172 g, 85%) containing ~13% impurity by NMR. The aldehyde was used with out further purification.

b) 4-((alpha-S)-alpha-((2S,5R)-2,5-Dimethyl-4-(3-fluorobenzyl)-1-piperazinyl)benzyl)-N,N-diethylbenzamide To a 500 mL three-necked flask was charged 5 g (24.3 mmol) of 4-formyl-N,N-diethylbenzamide (5.8 g @ 86% purity), 4.3 g (36.6 mmol) benzotriazole, 0.05 g (0.24 mmol) 4-toluenesulfonic acid, and 125 mL toluene. The mixture was heated to reflux removing water azeotropicly via a Dean-Stark trap. When water stopped accumulating in the trap, 5.4 g (24.3 mmol) of (2R,5S)-2,5-dimethyl-4-(3-fluorobenzyl)piperazine (IRIX Pharmaceuticals, Florence, S.C., U.S.A.) was added in 2–3 portions, removing water between additions. The reaction was refluxed until the theoretical amount of water was removed (2–3 h), followed by distillation of 100 mL of toluene from the reaction. The remaining solution was cooled below 60° C. Anhydrous tetrahydrofuran (150 mL) was added and the reaction was cooled below 10° C. Phenylmagnesium bromide (1 M in THF, 100 mL, 97.6 mmol) was charged while maintaining the temperature between 0 and 10° C. After stirring for two hours, the reaction was quenched by addition of 100 mL of saturated aqueous ammonium chloride. After phase separation, the aqueous layer was discarded. The organic layer was extracted with 3×75 mL of 1 N HCl. The aqueous layer was washed with 4×74 mL of methyl-tert.-butyl ether. The pH of the aqueous layer was raised to 8–10 with 115 mL 2 N sodium hydroxide. The aqueous layer was extracted with 3×75 mL of methyl-tert.-butyl ether. The organic layer was washed with brine, dried with Na$_2$SO$_4$ and evaporated under vacuum. The resulting solid was dissolved in 3 v/w of hot 2-propanol. Water was charged until a haze was observed. The solution was cooled with stirring to room temperature. The resulting solids were filtered and washed with 1/1 2-propanol-water (50 mL). The filter cake was dried at 40° C. to give 4.8 g (40%) of 4-((alpha-S)-alpha-((2S,5R)-2,5-dimethyl-4-(3-fluorobenzyl)-1-piperazinyl)benzyl)-N,N-diethylbenzamide as a white solid.

The following compounds were prepared by alkylation of 4-((alpha-S)-alpha-((2S,5R)-2,5-dimethyl-1-piperazinyl) benzyl)-N,N-diethylbenzamide (from Example 6, Method 1, intermediate (c)) with the appropriate benzyl halide in similar fashion to the process for Example 6, Method 1, procedure (d).

EXAMPLE 7

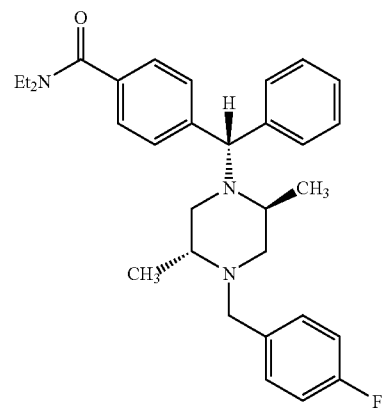

4-((alpha-S)-alpha-((2S,5R)-2,5-Dimethyl-4-(4-fluorobenzyl)-1-piperazinyl)benzyl)-N,N-diethylbenzamide (Yield 96.4%). Calc. for C$_{31}$H$_{38}$FN$_3$O: C, 76.35; H, 7.85; N, 8.62; F, 3.90. Found C, 76.32; H, 7.86; N, 8.60; F, 3.95%.

¹H NMR (CDCl3, 600 MHz); δ 1.07 (d, J=6.2 Hz, 3H); 1.10 (d, J=6.3 Hz, 3H, partially overlapped by br m, 3H); 1.23 (br m, 3H); 1.93 (m, 1H); 1.98 (dd, J=11.1, 8.3 Hz, 1H); 2.54 (br m, 2H); 2.65 (m, 2H); 3.14 (d, J=13.1 Hz, 1H); 3.28 (br m, 2H); 3.54 (br m, 2H); 3.86 (d, J=13.1 Hz, 1H); 5.15 (s, 1H); 6.90 (t, J=8.2 Hz, 2H); 7.20 (d, J=7.3 Hz, 2H); 7.24 (m, 2H); 7.27 (m, 1H; partially overlapped by CHCl3); 7.29 (d, J=9.4 Hz, 2H); 7.33 (m, 2H); 7.46 (d, J=8.1 Hz, 2H).

EXAMPLE 8

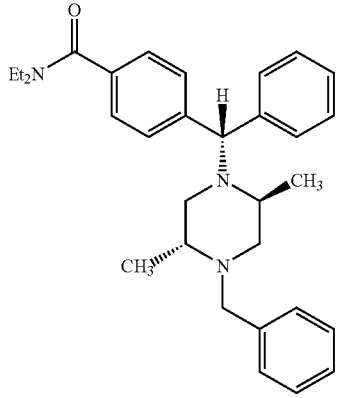

4-((alpha-S)-alpha-((2S,5R)-4-Benzyl-2,5-dimethyl-1-piperazinyl)benzyl)-N,N-diethylbenzamide (Yield 71.8%). Calc. for $C_{31}H_{39}N_3O$: C, 79.28; H, 8.37; N, 8.95. Found C, 79.05; H, 8.34; N, 8.91%. ¹H NMR (CDCl3, 500 MHz); δ 1.09 (d, J=6.2 Hz, 3H); 1.12 (d, J=6.1 Hz, 3H); both doublets partially overlapped by br m, 3H); 1.24 (br m, 3H); 1.72 (m, 1H); 1.93 (m, 1H); 2.02 (dd, J=9.3, 8.4 Hz, 1H); 2.55 (m, 2H); 2.66 (dd, J=11.1, 2.4 Hz, 1H); 2.70 (dd, J=11, 2.5 Hz, 1H); 3.18 (d, J=13.8 Hz, 1H); 3.28 (br m, 2H); 3.55 (br m, 2H); 3.92 (d, J=13.1 Hz, 1H); 5.18 (s, 1H); 7.20 (d, J=7.4 Hz, 2H, partially overlapped by m, 1H); 7.30 (m, 9H); 7.47 (d, J=8 Hz, 2H).

EXAMPLE 9

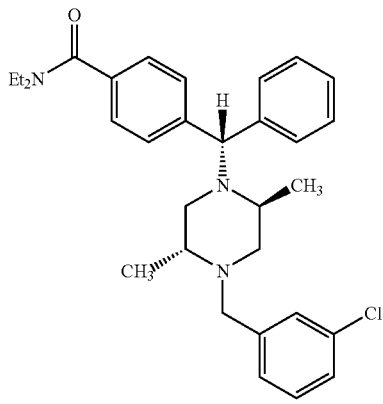

4-((alpha-S)-alpha-((2S,5R)-4-(3-Chlorobenzyl)-2,5-dimethyl-1-piperazinyl)benzyl)-N,N-diethylbenzamide (Yield 75.8%). Calc. for $C_{31}H_{38}ClN_3O$: C, 73.86; H, 7.60; N, 8.34; Cl, 7.03. Found C, 73.86; H, 7.68; N, 8.37; Cl, 7.01%. ¹H NMR (CDCl3, 600 MHz); δ 1.06 (d, J=6.2 Hz, 3H); 1.12 (d, J=6.1 Hz, 3H, overlapping br m, 3H); 1.23 (br m, 3H); 1.94 (br t, J=9.5 Hz, 1H); 2.01 (dd, J=11.1, 8.2 Hz, 1H); 2.56 (m, 2H); 2.67 (dt, J=10.5, 2.4 Hz, 2H); 3.15 (d, J=13.5 Hz, 1H); 3.28 (br m, 2H); 3.54 (br m, 2H); 3.86 (d, J=13.5 Hz, 1H); 5.15 (s, 1H); 7.19 (m, 5H); 7.29 (m, 4H); 7.33 (br t, J=7.4 Hz, 2H); 7.46 (d, J=8.1 Hz, 2H).

EXAMPLE 10

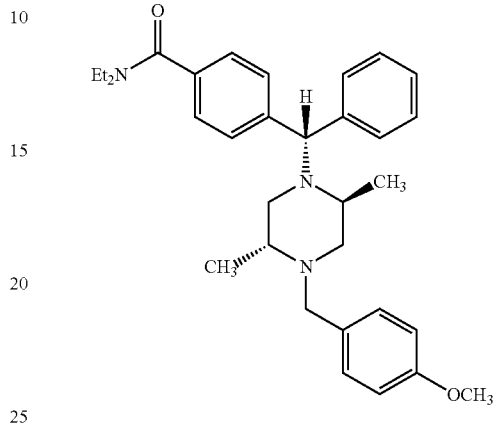

4-((alpha-S)-alpha-((2S,5R)-2,5-dimethyl-4-(4-methoxybenzyl)-1-piperazinyl)benzyl)-N,N-diethylbenzamide (Yield 72.44%). Calc. for $C_{32}H_{41}N_3O_2$: C, 76.92; H, 8.27; N, 8.41. Found C, 76.98; H, 8.38; N, 8.42%. ¹H NMR (CDCl3, 600 MHz); δ 1.07 (d, J=6.2 Hz, 3H); 1.11 (d, J=6.1 Hz, 3H, overlapping br m, 3H); 1.23 (br m, 3H); 1.91 (br t, J=10.2 Hz, 1H); 1.99 (dd, J=11.0, 8.6 Hz, 1H); 2.52 (br m, 2H); 2.64 (dd, J=11.5, 2.6 Hz, 1H); 2.68 (dd, J=11.1, 2.6 Hz, 1H); 3.13 (d, J=12.9 Hz, 1H); 3.28 (br m, 2H); 3.54 (br m, 2H); 3.79 (s, 3H); 3.85 (d, J=13.5 Hz, 1H); 5.17 (s, 1H); 6.82 (d, J=8.5 Hz, 2H); 7.19 (d, J=8.3 Hz, 4H); 7.29 (m, 5H); 7.46 (d, J=8.1 Hz, 2H).

EXAMPLE 11

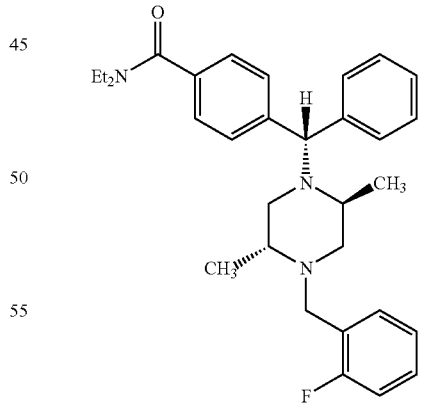

4-((alpha-S)-alpha-((2S,5R)-2,5-Dimethyl-4-(2-fluorobenzyl)-1-piperazinyl)benzyl)-N,N-diethylbenzamide (Yield 68.9%). Calc. for $C_{31}H_{38}FN_3O$: C, 76.35; H, 7.85; N, 8.62; F, 3.90. Found C, 76.35; H, 8.02; N, 8.60; F, 3.81%. ¹H NMR (CDCl3, 600 MHz); δ 1.09 (d, J=6.1 Hz, 3H); 1.13

(d, J=6.1 Hz, 3H); (both doublets overlapped by br m, 3H); 1.24 (br m, 3H); 1.90 (br t, J=10.4 Hz, 1H); 2.08 (dd, J=10.9, 8.6 Hz, 1H); 2.56 (br m, 2H); 2.66 (dd, J=11.5, 2.7 Hz, 1H); 2.73 (dd, J=11.1, 2.4 Hz, 1H); 3.28 (br m, 2H); 3.34 (d, J=13.8 Hz, 1H); 3.54 (br m, 2H); 3.88 (d, J=13.8 Hz, 1H); 5.19 (s, 1H); 7.00 (br t, J=9.1 Hz, 1H); 7.07 (t, J=7.5 Hz, 1H); 7.19 (m, 3H); 7.29 (m, 5H); 7.37 (br t, J=7.1 Hz, 1H); 7.46 (d, J=8.1 2H).

EXAMPLE 12

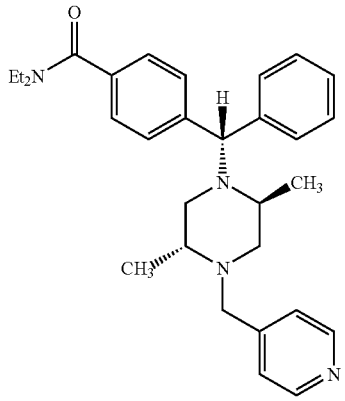

4-((alpha-S)-alpha-((2S,5R)-2,5-Dimethyl-4-(4-pyridylmethyl)-1-piperazinyl)benzyl)-N,N-diethylbenzamide (Yield 69.7%). Calc. for $C_{30}H_{38}N_4O$ 0.15 $H_2O$: C, 76.12; H, 8.16; N, 11.84. Found C, 76.14; H, 8.36; N, 11.70%. $^1$H NMR (CDCl3, 600 MHz); δ 1.05 (d, J=6.1 Hz, 3H); 1.11 (d, J=6.2 Hz, 3H; overlapped by br m, 3H); 1.24 (br m, 3H); 1.96 (br t, J=10.0 Hz, 1H); 2.08 (dd, J=7.8, 4.1 Hz, 1H); 2.59 (br d, J=4.9 Hz, 2H); 2.68 (m, 2H); 3.21 (d, J=14.0 Hz, 1H); 3.27 (br m, 2H); 3.54 (br m, 2H); 3.86 (d, J=14.2 Hz, 1H); 5.13 (s, 1H); 7.23 (d, J=7.4 Hz, 2H); 7.24 (d, J=5.6 Hz, 2H); 7.29 (d, J=8.2 Hz, 2H, partially obscuring doublet, 1H); 7.34 (br t, J=7.4 Hz, 2H); 7.46 (d, J=8.1 2H); 8.49 (d, J=5.9 Hz, 2H).

EXAMPLE 13

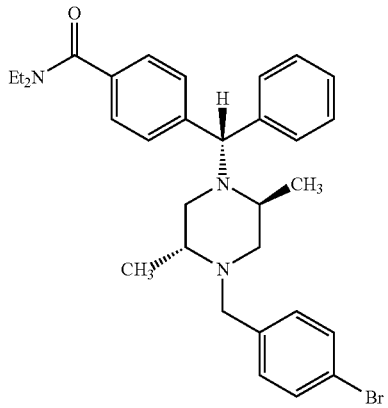

4-((alpha-S)-alpha-((2S,5R)-4-(4-Bromobenzyl)-2,5-dimethyl-1-piperazinyl)benzyl)-N,N-diethylbenzamide (Yield 89.87%). Calc. for $C_{31}H_{38}BrN_3O$: C, 67.87; H, 6.98; N, 7.66; Br, 14.57. Found C, 68.00; H, 7.02; N, 7.68; Br, 14.44%. $^1$H NMR (CDCl3, 600 MHz); δ 1.06 (d, J=6.2 Hz, 3H); 1.10 (d, J=6.1 Hz, 3H, overlapping br m, 3H); 1.23 (br m, 3H); 1.94 (br t, J=9.4 Hz, 1H); 2.01 (dd, J=11.1, 8.1 Hz, 1H); 2.54 (m, 2H); 2.65 (d, J=9.2 Hz, 2H); 3.13 (d, J=13.4 Hz, 1H); 3.27 (br m, 2H); 3.54 (br m, 2H); 3.83 (d, J=13.5 Hz, 1H); 5.15 (s, 1H); 7.17 (d, J=8.1 Hz, 2H); 7.21 (d, J=7.5 Hz, 2H); 7.27 (d, J=6.2 Hz, 1H, partially obscured by CHCl3); 7.29 (d, J=8.1 Hz, 2H); 7.32 (br t, J=7.4 Hz, 2H); 7.39 (d, J=8.3 Hz, 2H); 7.46 (d, J=8.1 Hz, 2H).

EXAMPLE 14

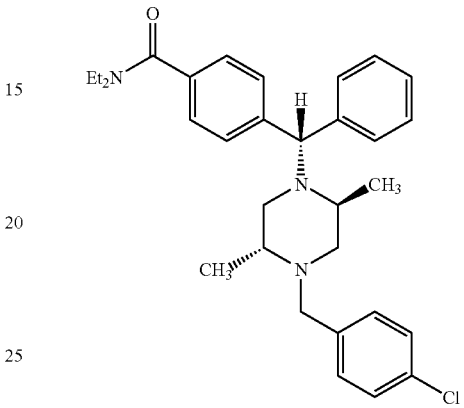

4-((alpha-S)-alpha-((2S,5R)-4-(4-Chlorobenzyl)-2,5-dimethyl-1-piperazinyl)benzyl)-N,N-diethylbenzamide (Yield 74.98%). Calc. for $C_{31}H_{38}ClN_3O$: C, 73.86; H, 7.60; N, 8.34; Cl, 7.03. Found C, 73.76; H, 7.65; N, 8.22; Cl, 7.07%. $^1$H NMR (CDCl3, 600 MHz); δ 1.06 (d, J=6.1 Hz, 3H); 1.10 (d, J=6.1 Hz, 3H, overlapping br m, 3H); 1.23 (br m, 3H); 1.92 (br t, J=9.2 Hz, 1H); 1.98 (dd, J=11.0, 8.3 Hz, 1H); 2.54 (m, 2H); 2.65 (d, J=11.2 Hz, 2H); 3.15 (d, J=13.3 Hz, 1H); 3.27 (br m, 2H); 3.54 (br m, 2H); 3.85 (d, J=13.2 Hz, 1H); 5.15 (s, 1H); 7.21 (m, 4H); 7.23 (d, J=7.2 Hz, 2H); 7.26 (m, 1H, partially obscured by CHCl3); 7.29 (d, J=8.0 Hz, 2H); 7.33 (br t, J=7.4 Hz, 2H); 7.46 (d, J=8.0 Hz, 2H).

EXAMPLE 15

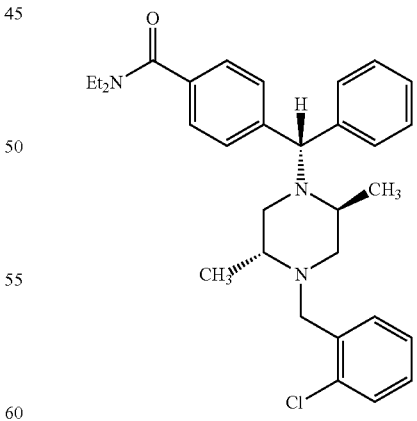

4-((alpha-S)-alpha-((2S,5R)-4-(2-Chlorobenzyl)-2,5-dimethyl-1-piperazinyl)benzyl)-N,N-diethylbenzamide (Yield 89.26%). Calc. for $C_{31}H_{38}ClN_3O$: C, 73.86; H, 7.60; N, 8.34; Cl, 7.03. Found C, 73.70; H, 7.66; N, 8.30; Cl, 7.14%. ¹H NMR (CDCl3, 600 MHz); δ 1.07 (d, J=6.1 Hz, 3H); 1.12 (d, J=6.3 Hz, 3H, overlapping br m, 3H); 1.23 (br m, 3H); 1.96 (m, 1H); 2.12 (dd, J=11.1, 7.8 Hz, 1H); 2.60 (m, 1H), partially superimposed on 2.67 (d, J=7.1 Hz, 1H); 2.76(dd, J=11.1, 2.3 Hz, 1H); 3.28 (br m, 2H); 3.38 (d, J=14.7 Hz, 1H); 3.54 (br m, 2H); 3.90 (d, J=14.5 Hz, 1H); 5.13 (s, 1H); 7.13 (dt, J=7.5, 1.3 Hz, 1H); 7.18 (t, J=7.4 Hz, 1H); 7.23 (d, J=7.4 Hz, 2H); 7.30 (d, J=8.2 Hz, 2H) superimposed on 7.30 (m, 2H); 7.33 (t, J=7.4 Hz, 2H); 7.48 (d, J=8.1 Hz, 2H) superimposed on 7.48 (m, 1H).

EXAMPLE 16

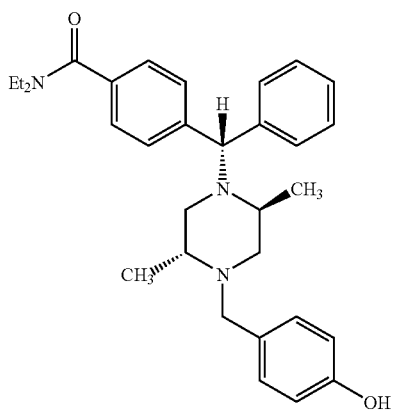

4-((alpha-S)-alpha-((2S,5R)-2,5-Dimethyl-4-(4-hydroxybenzyl)-1-piperazinyl)benzyl)-N,N-diethylbenzamide 4-Hydroxybenzaldehyde (488 mg, 4.0 mmol) was dissolved in a solution of 4-((alpha-S)-alpha-((2S,5R)-2,5-dimethyl-1-piperazinyl)benzyl)-N,N-diethylbenzamide (759 mg, 2.0 mmol, from Example 6, Method 1, intermediate (c)) and acetic acid in tetrahydrofuran (10 mL). Sodium triacetoxy borohydride (848 mg, ~4 mmol) was added portion wise over 5 min, then the reaction mixture sealed under nitrogen and stirred overnight at room temperature. The reaction mixture was evaporated to dryness and the residue partitioned between water (6 mL) and ethyl acetate (20 mL). The aqueous solution was further extracted with ethyl acetate (2×10 mL) and the combined extract and washings diluted with an equal volume of ether. The organic solution was extracted with 3M-HCl and the acidic aqueous solution carefully neutralized, initially with 5M-NaOH, then saturated NaHCO₃. At pH 4 the solution was filtered through a 0.45 mM syringe filter to remove a small quantity of an off-white gummy solid. The pH of the filtrate was adjusted to 8.5 to precipitate a flocculent white solid which was filtered off, washed well with cold water and dried overnight at 2 mm Hg at room temperature to yield 4-((alpha-S)-alpha-((2S,5R)-2,5-dimethyl-4-(4-hydroxybenzyl)-1-piperazinyl)benzyl)-N,N-diethylbenzamide (73.05%). Calc. for $C_{31}H_{39}N_3O_2$ 1.5$H_2O$ C, 72.62; H, 8.26; N, 8.20. Found C, 72.58; H, 7.83; N, 8.40. ¹H NMR (1% NaOD in D2O, 300 MHz); δ 0.75 (br m, 3H); 0.81 (br d, J=7.3 Hz, 6H); 0.94 (br m, 3H); 1.71 (m, 1H); 1.84 (m, 1H); 2.29 (m, 2H); 2.49 (br m, 2H); 2.91 (m, 3); 3.22 (m, 2H); 3.57 (br m, 2H); 5.02 (s, 1H); 6.39 (d, J=7.5 Hz, 2H); 6.80 (d, J=7.3 Hz, 2H); 7.01 (m, 7H); 7.17 (m, 2H).

EXAMPLE 17

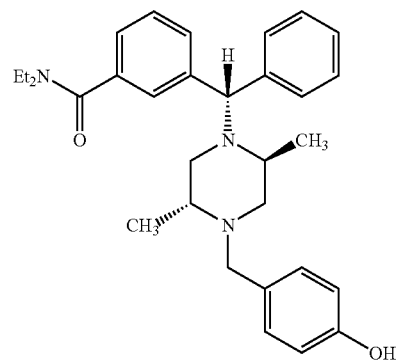

N,N-Diethyl-3-((S)-((2S,5R)-2,5-dimethyl-4-(4-hydroxybenzyl)piperazin-1-yl)(phenyl)methyl)benzamide 3-Carboxybenzaldehyde (150 g, 100 mmol) was weighed in a 250 mL, 3-necked, round bottom flask and stirred under nitrogen in 110 mL of toluene. Thionyl chloride (8.75 mL, 120 mmol) was added to the mixture, followed by the addition of 6 drops of dimethylformamide. A reflux condenser fitted with a calcium chloride drying tube was placed on the flask. The reaction was placed in an oil bath and heated at a bath temperature maintained below 120° C. The mixture was allowed to reflux for 1 hour after a clear solution was obtained and then cooled to room temperature. The solution was diluted with anhydrous toluene, and all volatiles were removed under vacuum.

The crude acid chloride was dissolved in 200 mL of dry tetrahydrofuran and cooled in an ice/water bath. Triethylamine (27.88 mL, 200 mmol) in 70 mL of dry tetrahydrofuran was added dropwise via an addition funnel, followed by diethylamine (10.45 mL, 100 mmol). The cloudy solution was allowed to warm to room temperature over 1 hour and stirred overnight. Water was added and the product was extracted with dichloromethane. The organic layer was washed with water and saturated sodium chloride solution and dried over sodium sulfate. The solvent was removed under vacuum to give 3-formyl-N,N-diethylbenzamide (17.72 g) as a light golden oil (86% crude yield). ¹H NMR (300 MHz, DMSO-d₆): δ 1.04–1.18 (m, 6H); 3.17–3.45 (m, 4H); 7.65–7.66 (m, 2H); 7.85 (s, 1H); 7.93–7.94 (m, 1H); 10.03 (s, 1H).

2R,5S-1-allyl-2,5-dimethylpiperazine (6.99 g, 45.30 mmol, Chirotech Technology, Ltd., Cambridge, England), benzotriazole (5.45 g, 45.76 mmol, 1.01 eq.), and 3-formyl-N,N-diethylbenzamide (9.30 g, 45.30 mmol) were mixed in 300 mL of dry toluene with two drops of triethylamine. The mixture was placed in an oil bath maintained below 140° C. (bath temperature. The flask was attached to a Dean-Stark trap and reflux condenser to allow the azeotropic removal of water. The mixture was refluxed for 2–3 hours, under a nitrogen atmosphere, then the majority of the toluene was removed under reduced pressure. The crude adduct was used in the following procedure without isolation. The crude benzotriazole adduct was dissolved in 200 mL of tetrahydrofuran and phenylmagnesium bromide (1 M in THF, 1.75 equiv.) was added via a syringe. After stirring under nitrogen at room temperature for 2 hours, the reaction was quenched with 20 mL of saturated ammonium chloride solution. After stirring for 30 min, a generous amount of anhydrous magnesium sulfate was added. Filtering and concentrating the solution under reduced pressure gave the crude product contaminated with benzotriazole. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure. The crude material was chromatographed on silica gel (20–25 g of silica gel per gram of crude material) eluting first with methylene chloride, then with 20% ethyl acetate in methylene chloride to remove the less polar contaminant. Then, the column was eluted with a solution of ethyl acetate containing 2% ammonium hydroxide (solution A) in a gradient with methylene chloride (solution B), quickly increasing in polarity from 25% to 100% (solution A in B). The desired fractions were combined and the solvent was removed under reduced pressure to give 5.52 g of (+)-3-((αR)-α-((2S,5R)-4-allyl-2,5-dimethyl-1-piperazinyl)benzyl)-N,N-diethylbenzamide was obtained as a golden oil. $^1$H NMR (300 MHz, CDCl$_3$): δ 0.96–0.98 (d, J=6.1 Hz, 3H); 0.98–1.15(m, 6H); 1.17–1.19(d, J=6.1 Hz, 3H); 1.80–1.85(t, 1H); 2.01–2.18 (m, 2H); 2.40–2.62 (m, 3H); 2.76–2.81 (m, 2H); 3.11–3.60 (m, 4H); 5.05–5.11 (dd, J$_1$=6.1 Hz, J$_2$=16.6 Hz, 2H); 5.16 (s, 1H); 5.75–5.90 (m, 1H); 7.14–7.17 (d, J=7.3 Hz, 1H); 7.21–7.47 (m, 8H).

The allyl portion was removed using Pd(dba)2/DPPB in the presence of thiosalicylic acid by the method of Genet [J. P. Genet, S. Lemaire-Audoire, M. Savignac, Tetrahedron Letters, 36, 1267–1270 (1995)]. The reaction was concentrated and the residue was dissolved in 50 mL ethyl acetate and 100 mL diethyl ether. After washing this with Na$_2$CO$_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried (Na2SO$_4$/MgSO$_4$) and concentrated under reduced pressure. The residual oil was purified by chromatography on silica gel (2% NH$_4$OH in EtOAc/CH$_2$Cl$_2$) to give 4.30 g (11.32 mmol) of a viscous, deep amber-orange colored oil.

The above free amine (0.46 g, 1.21 mmol) and 4-hydroxybenzaldehyde (0.30 g, 2.42 mmol) were placed in a 50 mL flask and sealed under nitrogen with 15 mL of tetrahydrofuran and 76.26 µl of acetic acid (1.33 mmol, 1.10 equiv). The reaction was stirred at room temperature for 20 minutes, and then sodium triacetoxyborohydride (0.51 g, 2.42 mmol) was added and stirred for 4 hours. The reaction solution was poured into 100 mL of ethyl acetate and washed with saturated NaHCO$_3$ (100 mL) and brine (80 mL). The solution was dried (Na$_2$SO$_4$/MgSO$_4$) and concentrated under reduced pressure. The residual light yellow oil was purified by chromatography on silica gel (EtOAc/CH$_2$Cl$_2$) to give 0.133 g (0.274 mmol) of the desired product as a white amorphous solid. The salt was made by dissolving the amine in ethanol and titrating to pH 3.92 with 0.2 M HCl in ethanol. The salt was redissolved in water and lyophilized to obtain a white powdery solid. $^1$H NMR (300 MHz, d$_6$-DMSO): δ 0.94–1.28 (m, 12H); 1.80–2.05 (m, 2H); 2.40–2.69 (m, 4H); 3.06–3.25 (m, 3H); 3.42–3.60 (d, J=6.5 Hz, 2H); 4.44–4.48 (d, J=14.2 Hz, 1H); 5.47 (s, 1H); 6.78–6.81 (d, 2H); 7.13–7.55 (m, 11H); 9.78 (s, 1H).

MS: 486.1 (M+1, 100%), 379.9 (10%).

Calculated for C$_{31}$H$_{39}$N$_3$O$_2$ 1.30 HCl & 1.10 H$_2$O: C, 67.35; H, 7.75; N, 7.60; Cl, 8.34. Found: C, 67.37; H, 7.64; N, 7.47; Cl, 8.20.

EXAMPLE 18

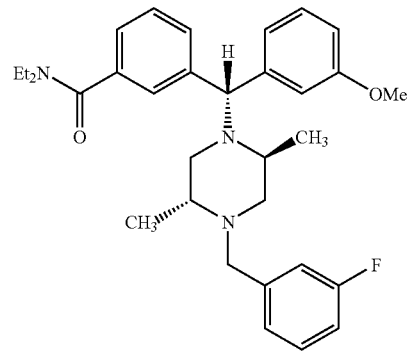

N,N-Diethyl-3-((R)-((2S,5R)-2,5-dimethyl-4-(3-fluorobenzyl)piperazin-1-yl)(3-methoxyphenyl)methyl)-benzamide 2R,5S-1-allyl-2,5-dimethylpiperazine (9.08 g, 58.85 mmol, Chirotech Technology, Ltd., Cambridge, England), benzotriazole (7.08 g, 59.44 mmol, 1.01 eq), and 3-formyl-N,N-diethylbenzamide (12.08 g, 58.85 mmol, Example 17) were mixed in 350 mL of dry toluene with twenty drops of triethylamine. The mixture was placed in an oil bath maintained below 140° C. (bath temperature). The flask was attached to a Dean-Stark trap and reflux condenser to allow the azeotropic removal of water. The mixture was refluxed for 4 hours, under a nitrogen atmosphere, then the majority of the toluene was removed under reduced pressure. The crude adduct was used in the following procedure without isolation.

The crude benzotriazole adduct was dissolved in 200 mL of tetrahydrofuran and 100 mL of 3-methoxyphenylmagnesium bromide (1 M in THF, 1.70 equiv.) was added via a double-ended needle. The reaction was slightly exothermic. Cooling in a room temperature water bath gave a cloudy, yellow-brown reaction mixture. After stirring under nitrogen at room temperature for 2 hours, the reaction was quenched with 15 mL of saturated ammonium chloride solution. After stirring for 30 min, a generous amount of anhydrous magnesium sulfate was added. Filtering and concentrating the solution under reduced pressure gave the crude product contaminated with benzotriazole. This residue was dissolved in ethyl acetate and extracted with 10% aqueous NaOH solution three times to remove most of the benzotriazole. The organic layer was washed with saturated sodium chloride solution, dried over sodium sulfate/magnesium sulfate, and the ethyl acetate was removed under reduced pressure.

The crude material was chromatographed on silica gel column eluting first with methylene chloride, then with 10% ethyl acetate in methylene chloride to remove the less polar contaminant. Then, the column was eluted with a solution of ethyl acetate. The desired fractions were combined and the solvent was removed under reduced pressure to give 15.47 g of 3-((αR)-α-((2S,5R)-4-allyl-2,5-dimethyl-1-piperazinyl)-3-methoxybenzyl)-N,N-diethylbenzamide as a golden oil. $^1$H NMR (300 MHz, CDCl$_3$): δ 0.96–1.26 (m, 12H); 1.86–1.92(m, 1H); 2.07–2.14 (m, 1H); 2.36–2.45 (m, 1H); 2.57–2.59 (m, 2H); 2.62–2.86 (m, 2H); 3.23–3.53 (m, 5H); 3.77 (s, 3H); 5.11–5.22 (m, 3H); 5.76–5.91 (m, 1H); 6.71–6.81 (m, 3H); 7.20–7.33 (m, 5H).

The allyl portion was removed using Pd(dba)2/DPPB in the presence of thiosalicylic acid by the method of Genet [J. P. Genet, S. Lemaire-Audoire, M. Savignac, Tetrahedron Letters, 36, 1267–1270 (1995)]. The reaction was concentrated and the residue was dissolved in 50 mL ethyl acetate and 100 mL diethyl ether. After washing this with $Na_2CO_3$ solution (3×100 mL) and water (1×100 mL), the organic solution was extracted with 3 N HCl (3×20 mL) and 1 N HCl (1×20 mL). The acidic extract was adjusted to pH 8.5 using NaOH solution and extracted with dichloromethane (3×25 mL). The solution was dried ($Na_2SO_4$/$MgSO_4$) and concentrated under reduced pressure. The residual oil was purified by chromatography on silica gel (2% $NH_4OH$ in EtOAc/$CH_2Cl_2$) to give 8.65 g (21.12 mmol) of a viscous, deep amber-orange colored oil.

A solution of 3-((αR)-α-((2S,5R)-2,5-dimethyl-1-piperazinyl)-3-methoxybenzyl)-N,N-diethylbenzamide (0.49 g, 1.20 mmol) in acetonitrile (10 mL) was added to sodium iodide (100 mg), sodium carbonate (0.70 g, 6.64 mmol) and stirred under nitrogen at room temperature during the addition of 3-fluorobenzyl bromide (0.16 mL, 1.32 mmol). The reaction was complete in 3 hours. The solvent was removed by evaporation and the residue was partitioned between methylene chloride and water. The aqueous layer was extracted with methylene chloride twice more, and the combined organic extracts were dried ($Na_2SO_4$/$MgSO_4$) and concentrated under reduced pressure. The residual brown oil was purified by chromatography on silica gel (EtOAc/$CH_2Cl_2$) to give 0.37 g (0.71 mmol) of the desired product as a light brown amorphous solid. The salt was made by dissolving the amine in ethanol and titrating to pH 3.92 with 0.2 M HCl in ethanol. The salt was redissolved in water and lyophilized to obtain a light brown powdery solid. $^1H$ NMR (300 MHz, $CDCl_3$): δ 1.04–1.22 (m, 12H); 1.93–2.08 (m, 2H); 2.51–2.76 (m, 5H); 3.10–3.60 (m, 4H); 3.78 (s, 3H); 3.84–3.89 (d, J=13.3 Hz, 1H); 5.11 (s, 1H); 6.76–7.46 (m, 12H).

MS: 518.0 (M+1, 60%), 296.0 (100%), 221.1 (60%).

Calculated for $C_{32}H_{40}FN_3O_2$·0.8 HCl: C, 70.28; H, 7.52; N, 7.68; F, 3.47. Found: C, 70.19; H, 7.47; N, 7.62; F, 3.26.

EXAMPLE 19

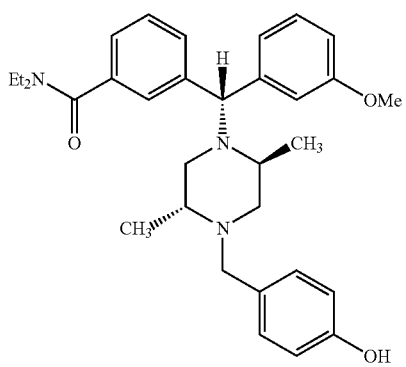

N,N-Diethyl-3-((R)-((2S,5R)-2,5-dimethyl-4-(4-hydroxybenzyl)piperazin-1-yl)(3-methoxyphenyl)methyl)-benzamide The title compound is made in identical fashion to the compound of Example 17 by substituting phenylmagnesium bromide with 3-methoxyphenyl magnesium bromide.

EXAMPLE 20

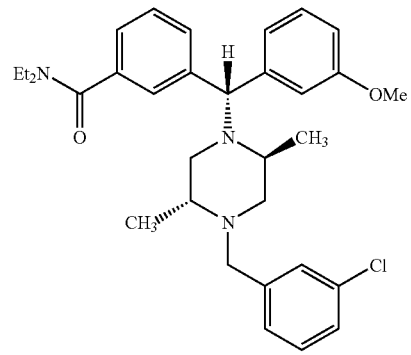

N,N-Diethyl-3-((R)-((2S,5R)-4-(3-chlorobenzyl)-2,5-dimethylpiperazin-1-yl)(3-methoxyphenyl)methyl)benzamide The title compound is made in identical fashion to the compound of Example 18 by substituting 3-fluorobenzyl bromide with 3-chlorobenzyl bromide.

EXAMPLE 21

The antidepressant-like activity of compounds of the present invention was demonstrated by the forced swim test in rats, as set forth below. The modified, Porsolt forced swim test has been extensively used to evaluate antidepressant-like activity of medicinal compounds. The Porsolt test was chosen as an assay because of its strong correlation between a test compound's effect on immobility time-shortening activity and antidepressant activity in a rodent model and the antidepressant effect in humans.

The forced swim test was originally described by Porsolt [*Eur. J. Pharmacology*, 47, 379–391(1978)] and subsequently modified by Lucki [*Psychopharmacol.*, 119, 47–54 (1995)]. Swim sessions were conducted by placing rats (five-week old male Sprague-Dawley rats may be used) in plastic containers measuring 20 cm in diameter, 46 cm in height and filled to a depth of 30 cm with tap water at 23° C.–25° C. This water depth was sufficient to prevent the rat from touching the bottom with its hind limbs or tail or escape due to the tube height.

Two swim sessions were conducted for each testing rodent, a 15 min habituation swim, during which the test subject learned that the tube was 'inescapable', and a 5 min test session 24 hours later. The test session was videotaped for later scoring of escape and immobility behaviors. The 5 minute test session was divided into 5 second time bins and the predominant behavior was recorded for each 5 sec bin (total 60 behavioral 'counts'). The behaviors scored were: swimming (exploration and investigation of escape possibilities); climbing (attempting to scale the tube walls by raising forelimbs out of water simultaneously and pawing at the tube); and immobility (limited or no movement of the fore limbs—making only those movements necessary to remain afloat with hind limbs).

The compounds of the present invention were administered by several routes including subcutaneously (s.c.), orally (p.o.), and intravenously (i.v.). Drugs with antidepressant-like activity decreased the number of time bins spent immobile (immobile counts) and increased the number of active escape behavior counts (swimming and/or climbing). The only procedural difference between oral, subcutaneous and intravenous dosing was that of pretreatment time (subcutaneously and orally=1 hr prior to test swim; intravenous=30 minutes prior to test swim). Control groups were administered the relevant vehicle solution used to dissolve the compound tested. Positive controls were run using known antidepressant compounds including desipramine and buprorion.

Where the group variance was not different between test and vehicle groups, pair wise comparison was made using a Student's T-test. Where the variance was significantly different between control and test groups, a Mann-Whitney U Test was used for pair wise comparison.

The compounds of the present invention were unexpectedly found to be active in the forced swim assay by decreasing immobility and increasing swimming and/or climbing activity. These results are similar to the results found in known antidepressants when tested in the forced swim test. It is believed that the results of increased activity and decreased immobility were mediated through at least the delta opioid receptor, because it was shown that the results exhibited in the forced swim test were blocked by the delta opioid receptor antagonist naltrindole (data not shown). These results provide statistically significant evidence that the present compounds, administered by multiple routes, possessed antidepressant activity.

Interestingly and unexpectedly some of the compounds of the present invention caused an increase in both swimming and climbing activity. Moreover, compounds of the present invention were found to be effective as an antidepressant by oral administration and at low dosages from about 1 to about 10 mg/kg, as shown below in Table 1.

TABLE 1

| Ex No | Compound | Dose (route) | Swimming counts | Climbing counts | Immobile counts |
|---|---|---|---|---|---|
| 1 | [structure] | 10 mg/kg (s.c.) | 6.00 ± 2.03 | 22.17 ± 4.08* | 31.83 ± 4.44* |
|   |   | 30 mg/kg (s.c.) | 3.40 ± 1.08* | 17.40 ± 3.61* | 39.20 ± 3.88* |
| 7 | [structure] | 10 mg/kg (i.v.) | 9.67 ± 1.76 | 22.50 ± 1.41* | 26.83 ± 2.32* |
|   |   | 30 mg/kg (i.v.) | 12.00 ± 3.42 | 23.75 ± 3.57* | 24.25 ± 3.50* |
| 4 | [structure] | 10 mg/kg (p.o.) | 29.4 ± 2.9* | 10.1 ± 1.6 | 20.5 ± 3.5* |
|   |   | 30 mg/kg (p.o.) | 32.3 ± 3.7* | 10.3 ± 2.5 | 17.4 ± 3.7* |

TABLE 1-continued

| Ex No | Compound | Dose (route) | Swimming counts | Climbing counts | Immobile counts |
|---|---|---|---|---|---|
| 2 | (structure: Et₂N-C(O)-phenyl-CH(H)-(3-hydroxyphenyl) attached to N of 2,5-dimethylpiperazine, other N bearing 3-fluorobenzyl) | 1 mg/kg (p.o.)<br>3 mg/kg (p.o.) | 13.9 ± 2.3<br>25.9 ± 2.5* | 16.9 ± 4.1*<br>9.5 ± 1.6* | 29.2 ± 5.4*<br>24.6 ± 3.3* |
| 3 | (structure: Et₂N-C(O)-phenyl-CH(H)-(3-hydroxyphenyl) attached to N of 2,5-dimethylpiperazine, other N bearing 2-fluorobenzyl) | 3 mg/kg (p.o.)<br>10 mg/kg (p.o.) | 19.8 ± 3.8*<br>33.4 ± 3.3* | 7.3 ± 1.6<br>8.4 ± 0.7 | 32.9 ± 5.1*<br>18.2 ± 3.8* |
| 5 | (structure: Et₂N-C(O)-phenyl-CH(H)-(3-methoxyphenyl) attached to N of 2,5-dimethylpiperazine, other N bearing 4-fluorobenzyl) | 10 mg/kg (p.o.)<br>30 mg/kg (p.o.) | 22.9 ± 4.0*<br>26.2 ± 3.9* | 10.0 ± 3.5<br>8.7 ± 2.2 | 27.1 ± 4.3*<br>25.1 ± 5.0* |

*$P < 0.05$ compared to vehicle control.

While the invention has been described herein in reference to specific aspects, features and illustrative embodiments of the invention, it will be appreciated that the utility of the invention is not thus limited, but rather extends to and encompasses numerous other aspects, features and embodiments. Accordingly, the claims hereafter set forth are intended to be correspondingly broadly construed, as including all such aspects, features and embodiments, within their spirit and scope.

We claim:

1. A method of combating depression in a subject experiencing or susceptible to same, comprising administering to said subject an effective amount of a therapeutic composition, wherein the composition comprises an active agent, wherein the active agent consists of at least one compound selected from the group consisting of:
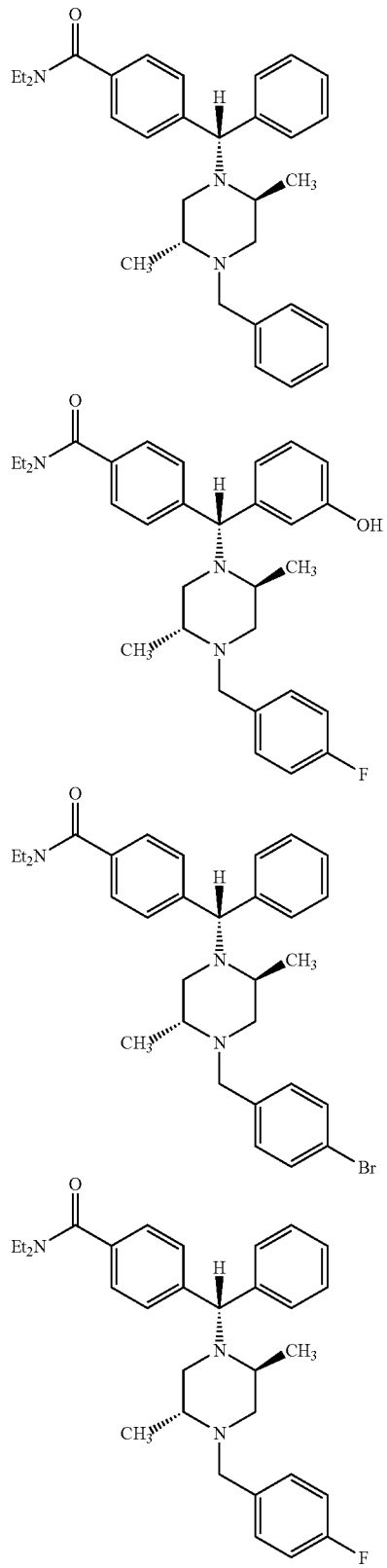
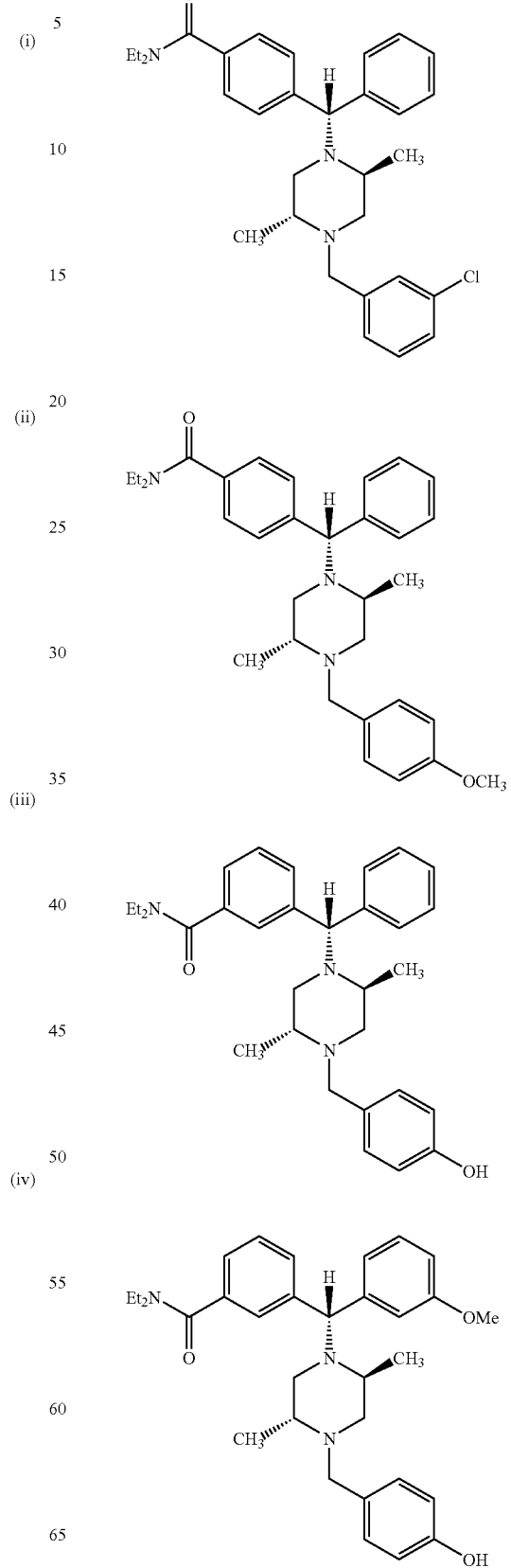

-continued
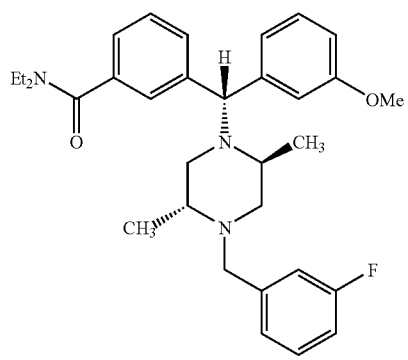
(ix)
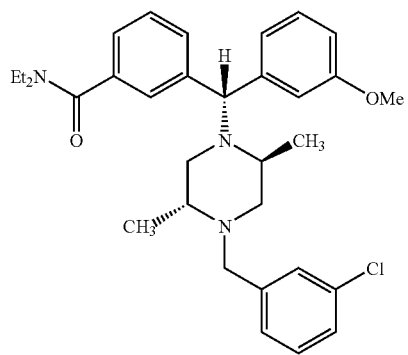
(x)
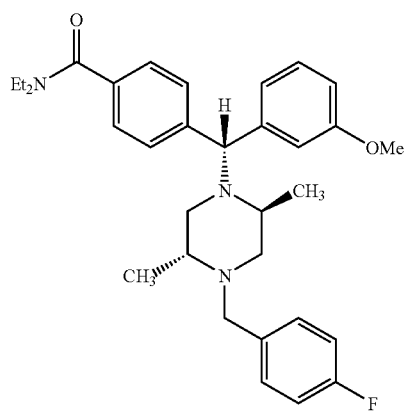
(xi)
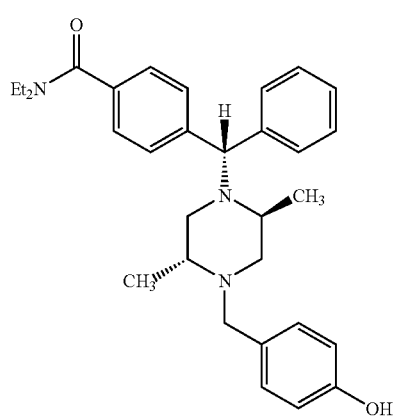
(xii)
-continued
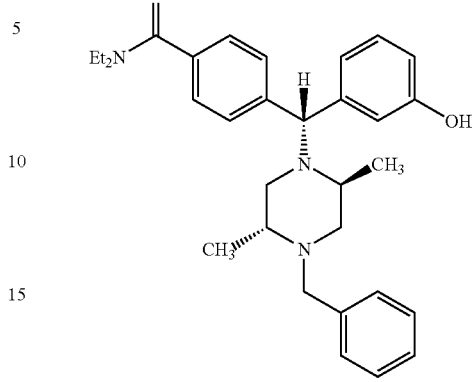
(xiii)
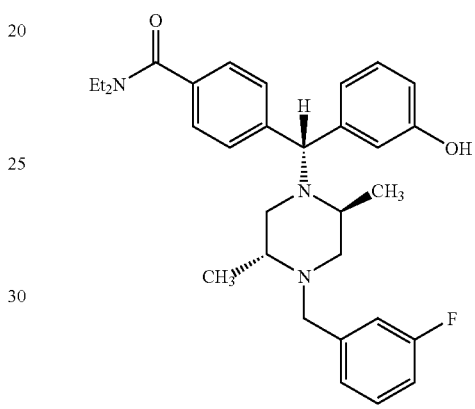
(xiv)
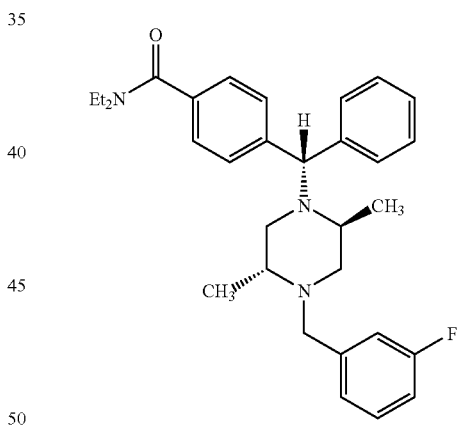
(xv)
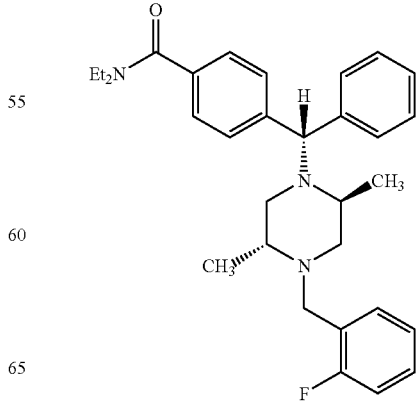
(xvi)

-continued (xvii)
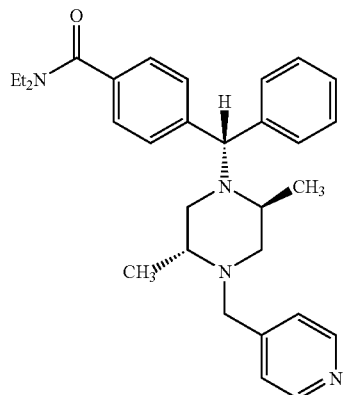

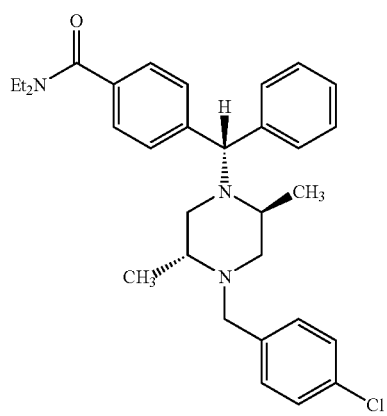

(xviii)

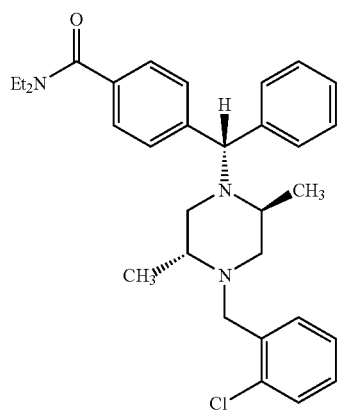

(xix)

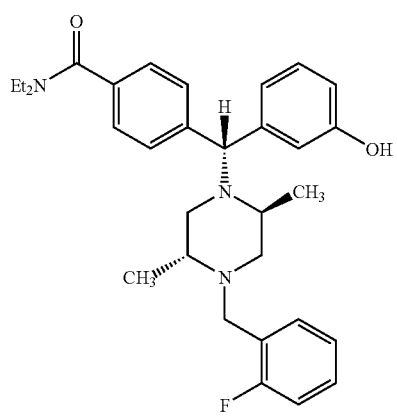

(xx)

-continued (xxi)
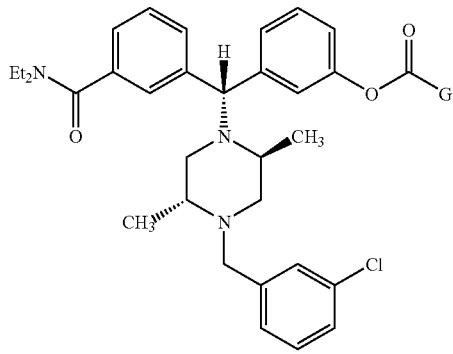

where G=O-alkyl, N(alkyl)₂, and any other pharmaceutically acceptable esters thereof;

and pharmaceutically acceptable salts and esters thereof.

2. A method of combating a mood disorder in a subject experiencing or susceptible to same, comprising administering to said subject an effective amount of a therapeutic composition comprising an active agent, wherein the active agent is at least one compound selected from the group consisting of:

(ii)
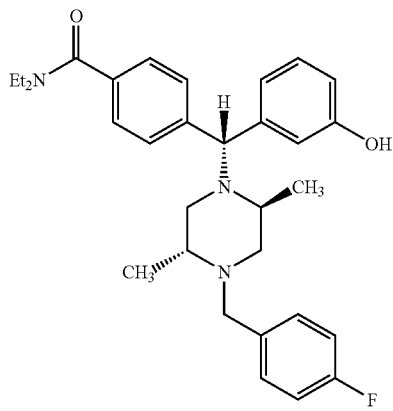

(iv)
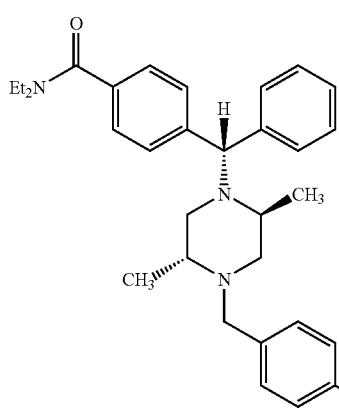

-continued
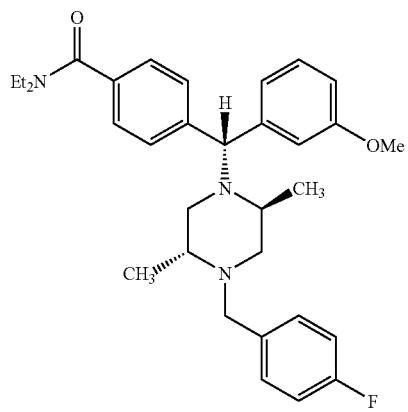
(xi)
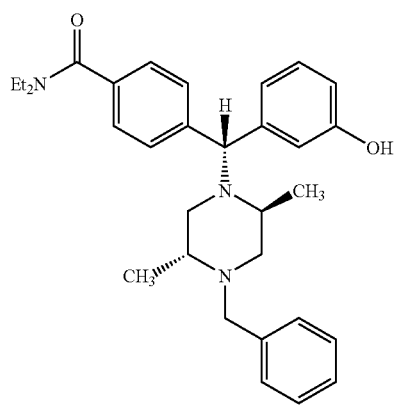
(xiii)
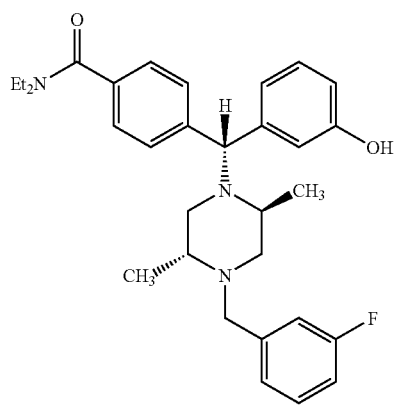
(xiv)
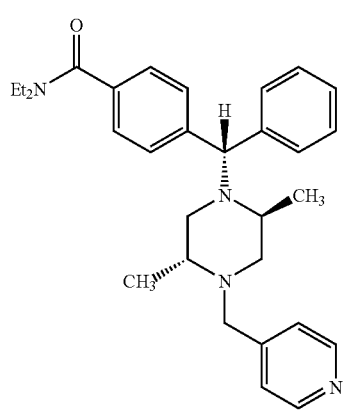
(xvii)
-continued
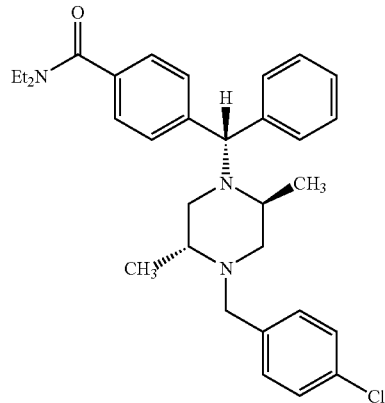
(xviii)
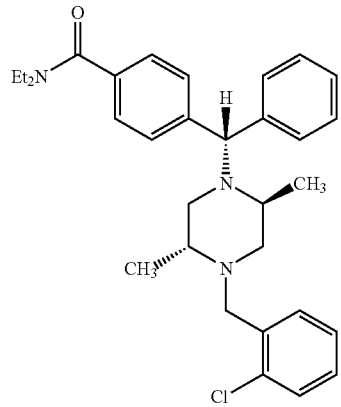
(xix)
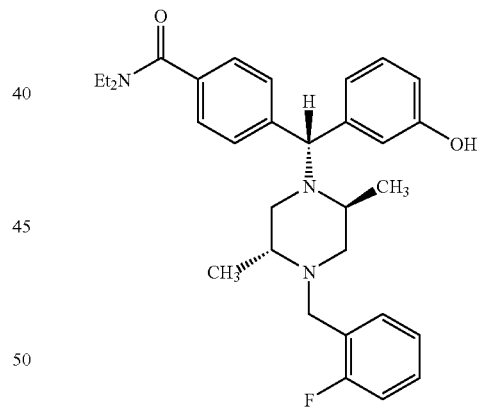
(xx)
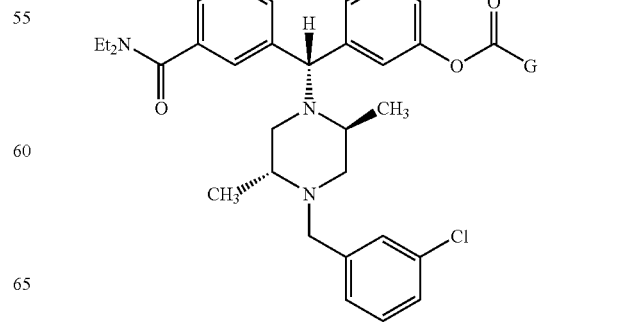
(xxi)

(xvii) 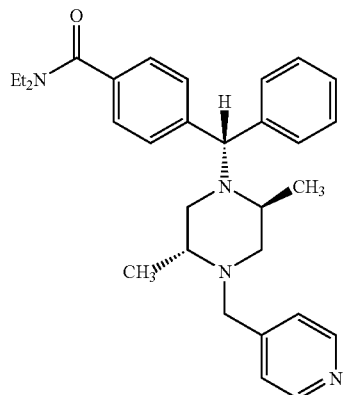

(xviii) 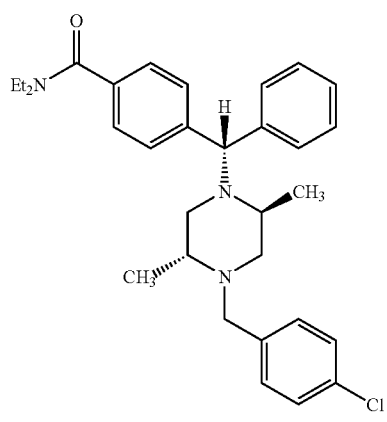

(xix) 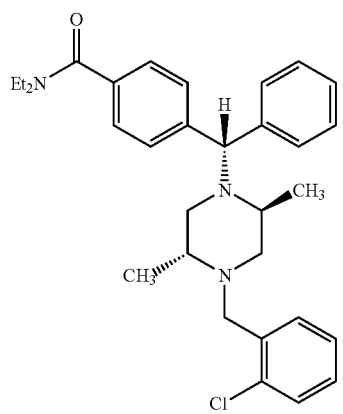

(xx) 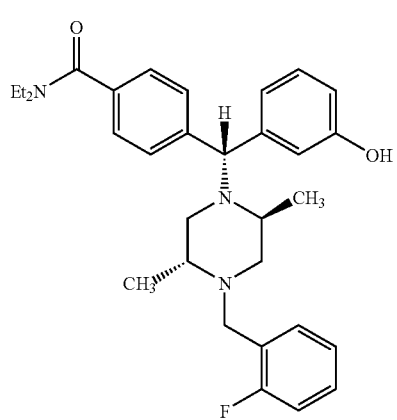

(xxi) 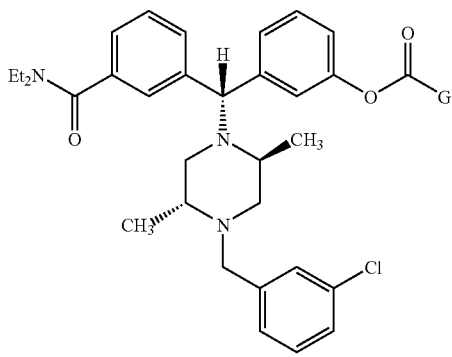

and pharmaceutically acceptable salts and esters thereof, wherein said mood disorder comprises depression, bipolar manic depression or seasonal affective disorder.

3. A method of combating a mood disorder in a subject experiencing or susceptible to same, comprising administering to said subject an effective amount of a therapeutic composition comprising an active agent, wherein the active agent consists of at least one compound selected from the group consisting of:

(i)

(ii)

-continued
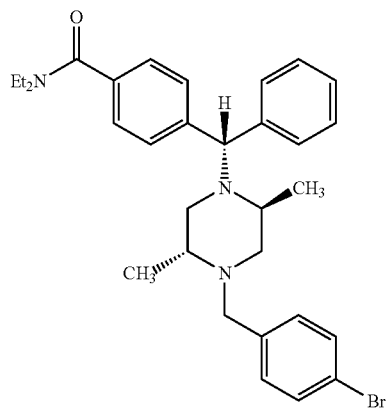
(iii)
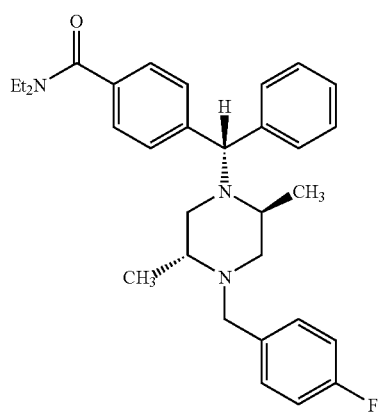
(iv)
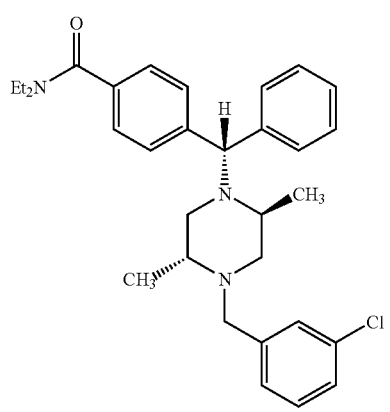
(v)
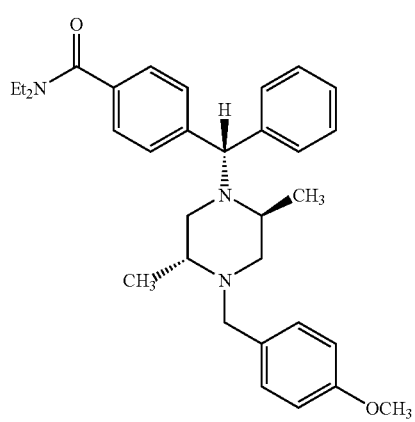
(vi)
-continued
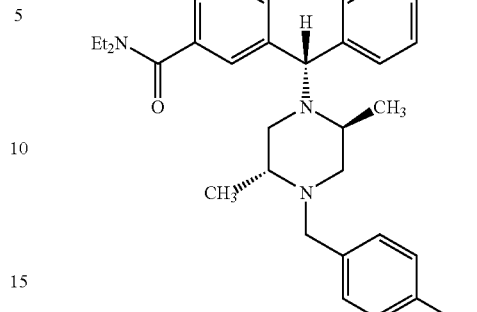
(vii)
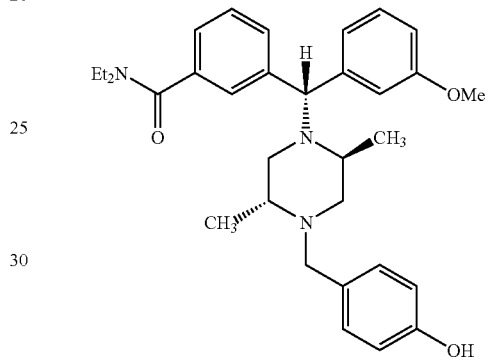
(viii)
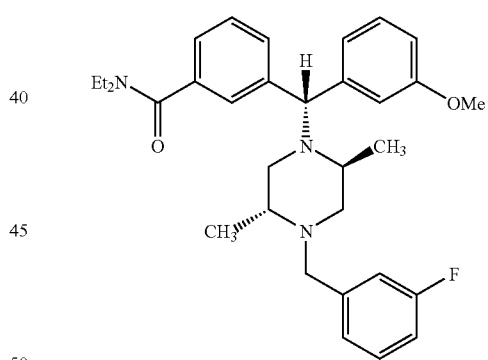
(ix)
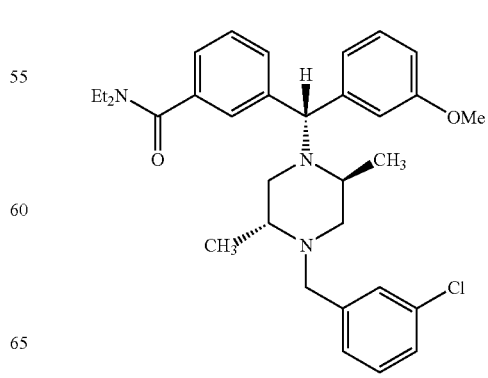
(x)

-continued
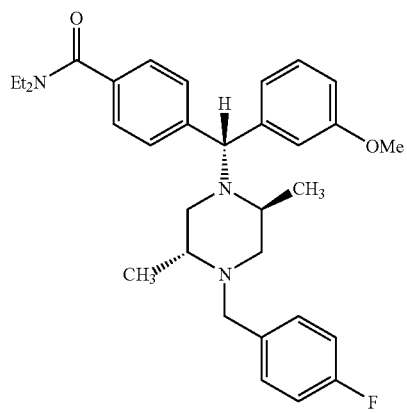
(xi)
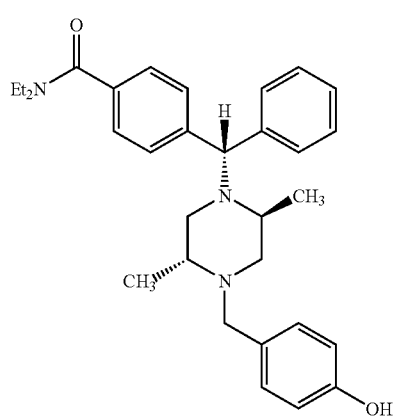
(xii)
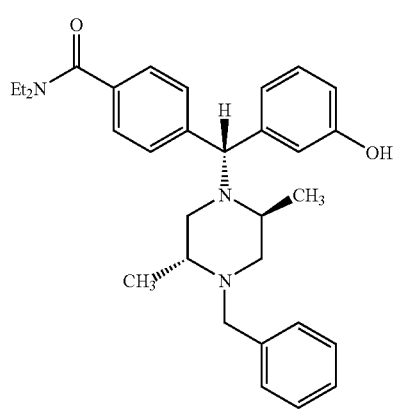
(xiii)
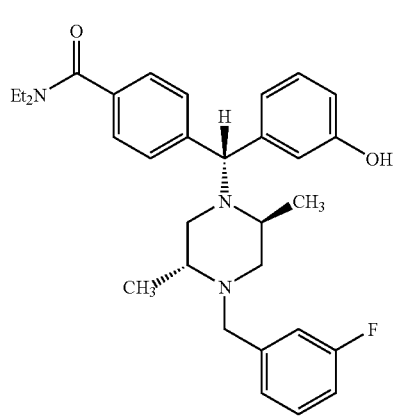
(xiv)
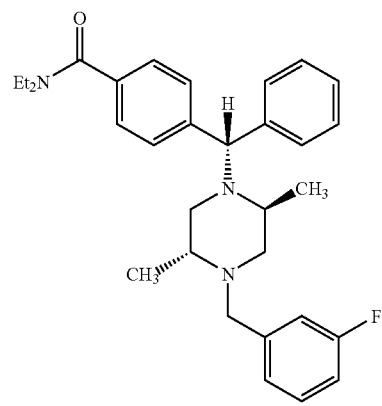
(xv)
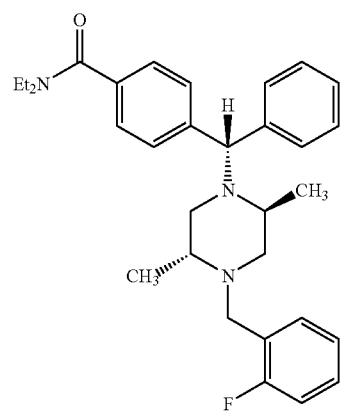
(xvi)
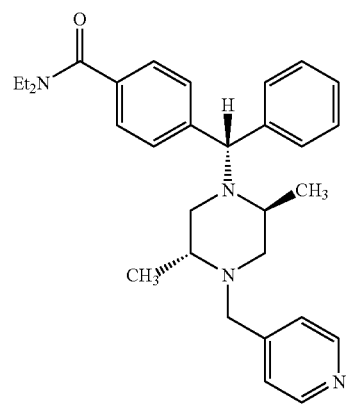
(xvii)
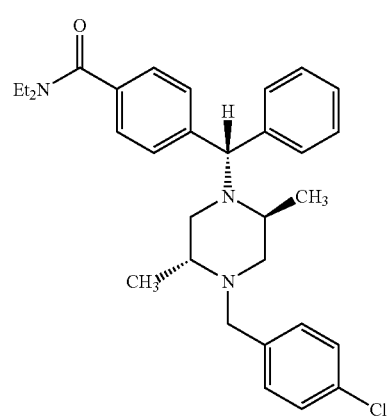
(xviii)

-continued

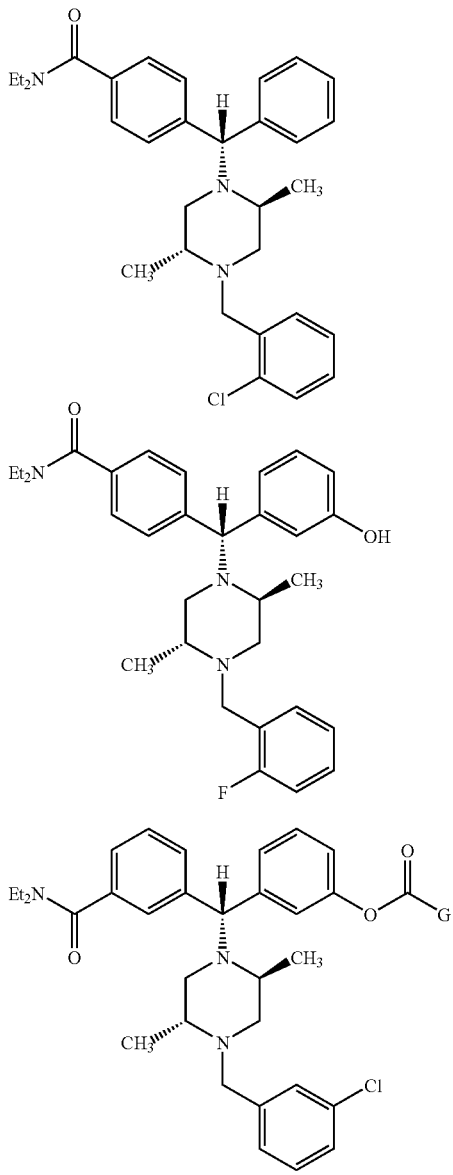

(xix)

(xx)

(xxi)

where G=O-alkyl, N(alkyl)$_2$, and any other pharmaceutically acceptable esters thereof;

and pharmaceutically acceptable salts and esters thereof, wherein the mood disorder comprises depression, bipolar manic depression or seasonal affective disorder.

4. The method of claim 3, wherein said therapeutic composition is administered by an administration modality selected from the group consisting of oral, rectal, topical, sub-lingual, mucosal, nasal, ophthalmic, subcutaneous, intramuscular, intravenous, transdermal, spinal, intrathecal, intra-articular, intra-arterial, sub-arachnoid, bronchial, lymphatic, and intra-uterine administration.

5. A method for combating depression, bipolar manic depression or seasonal affective disorder in a subject experiencing or susceptible to same, comprising: affixing a patch to a corporeal locus containing a composition for combating depression, bipolar manic depression or seasonal affective disorder in a subject experiencing or susceptible to same, the composition comprising an active agent, wherein the active agent consists of a member selected from the group consisting of:

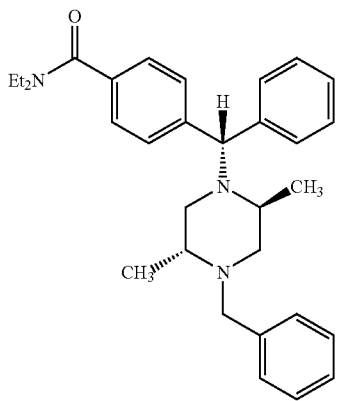

(i)

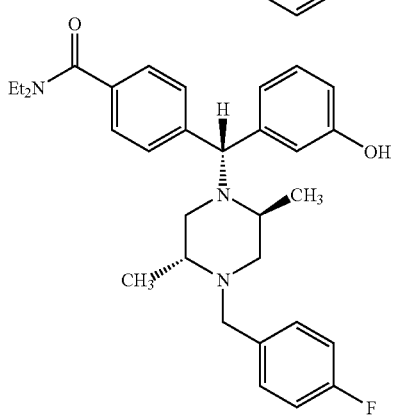

(ii)

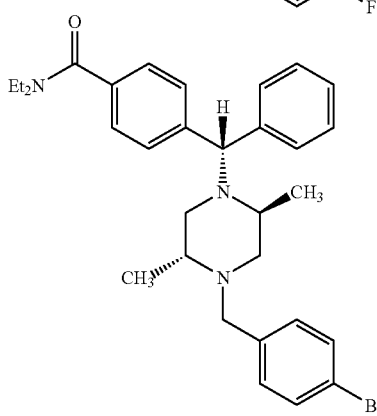

(iii)

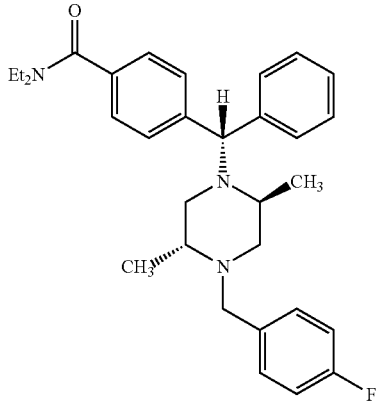

(iv)

-continued
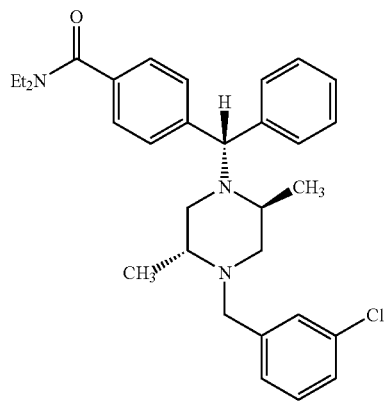
(v)
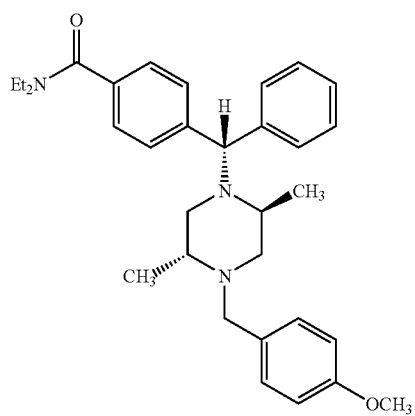
(vi)
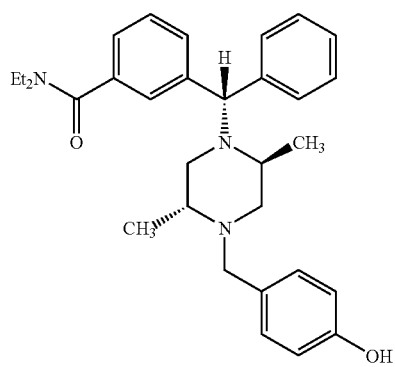
(vii)
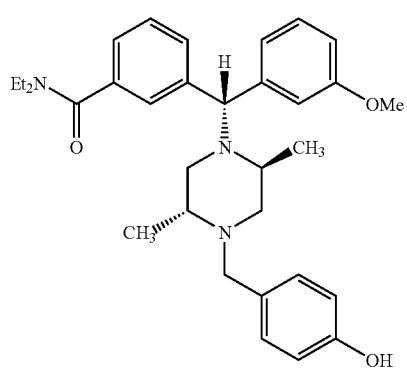
(viii)
-continued
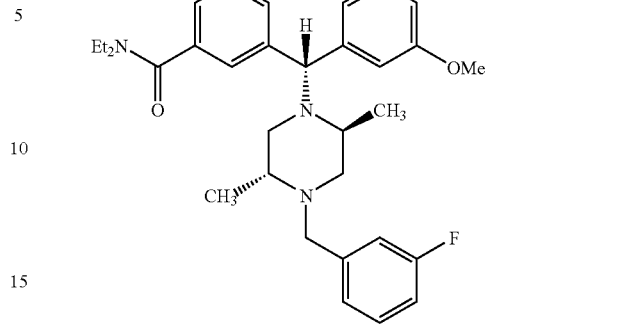
(ix)
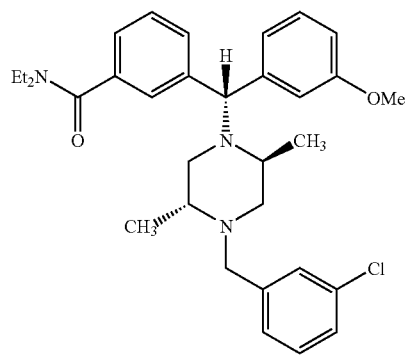
(x)
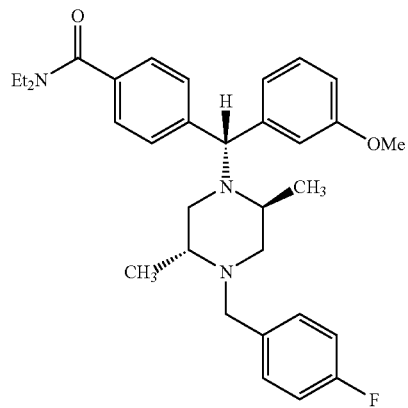
(xi)
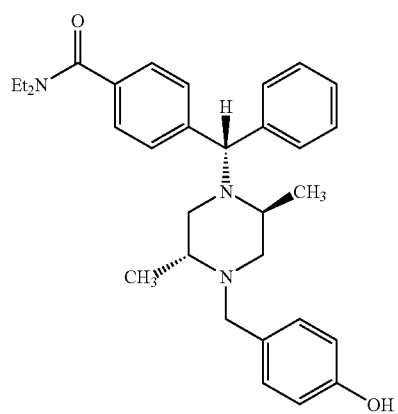
(xii)

-continued
(xiii)
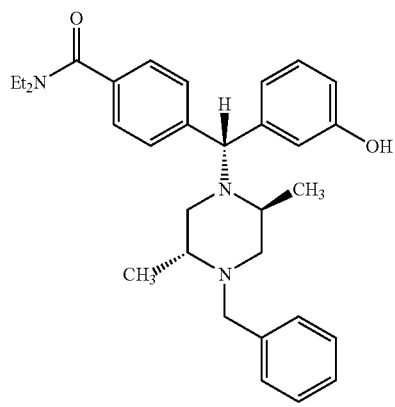
(xiv)
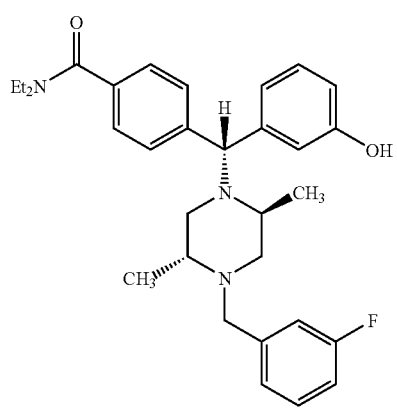
(xv)
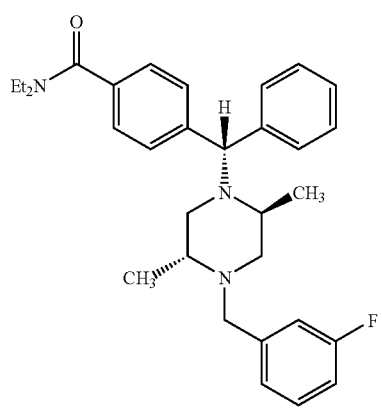
(xvi)
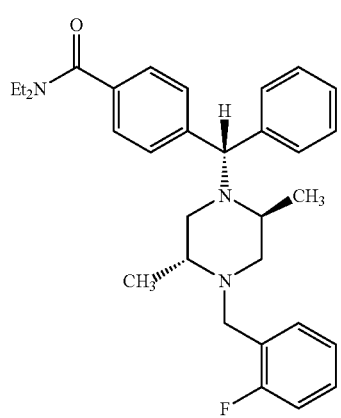
-continued
(xvii)
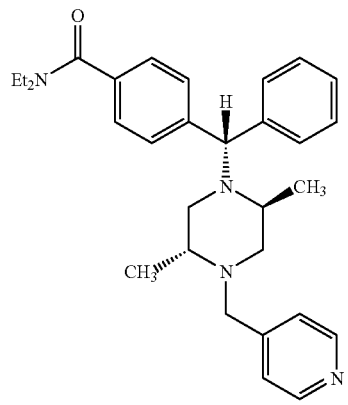
(xviii)
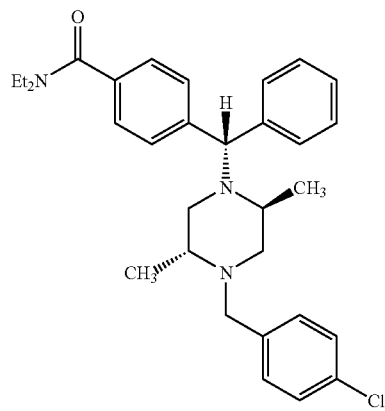
(xix)
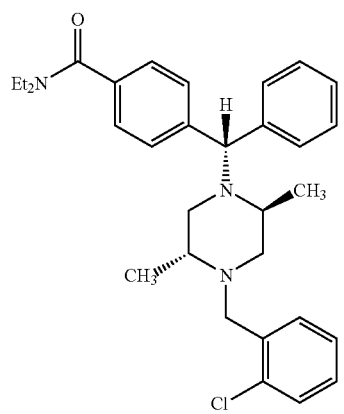
(xx)
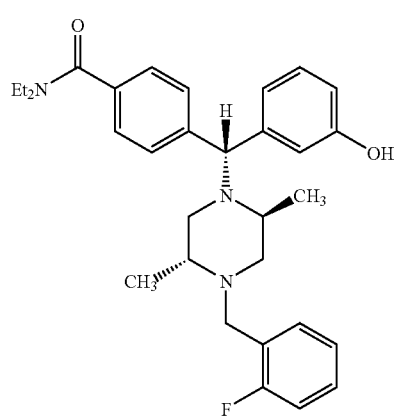

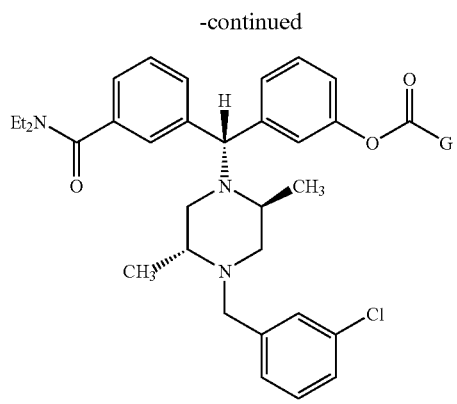

(xxi)

where G=O-alkyl, N(alkyl)₂, and any other pharmaceutically acceptable esters thereof;

and pharmaceutically acceptable salts and esters thereof.

6. The method of claim 5, wherein said patch comprises a transdermal patch.

7. The method of claim 5, wherein said patch comprises a transmucosal patch.

8. A method of combating depression, bipolar manic depression or seasonal affective disorder in a subject experiencing or susceptible to same, comprising administering to said subject an effective amount of a therapeutic composition comprising an active agent, wherein the active agent consists of a diarylmethylpiperazine compound of the formula:

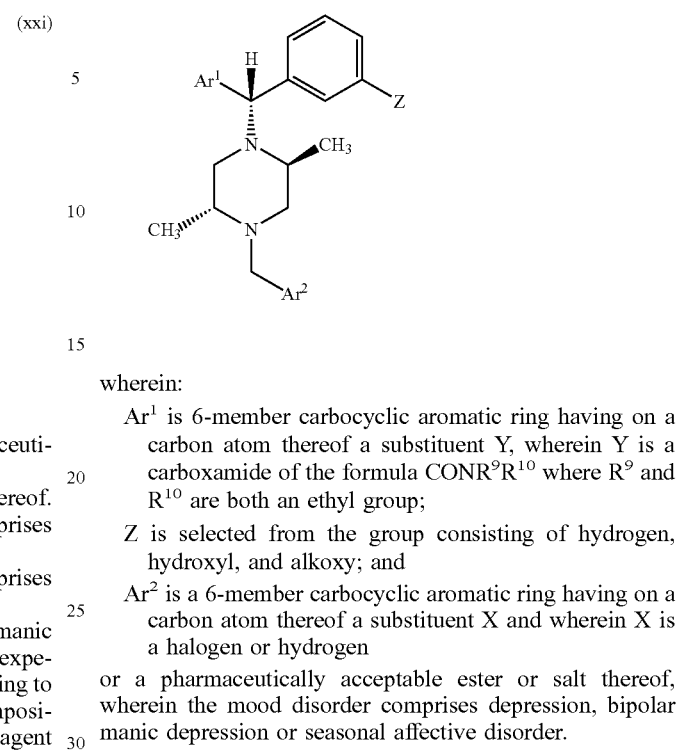

wherein:

Ar¹ is 6-member carbocyclic aromatic ring having on a carbon atom thereof a substituent Y, wherein Y is a carboxamide of the formula $CONR^9R^{10}$ where $R^9$ and $R^{10}$ are both an ethyl group;

Z is selected from the group consisting of hydrogen, hydroxyl, and alkoxy; and

Ar² is a 6-member carbocyclic aromatic ring having on a carbon atom thereof a substituent X and wherein X is a halogen or hydrogen or a pharmaceutically acceptable ester or salt thereof, wherein the mood disorder comprises depression, bipolar manic depression or seasonal affective disorder.

* * * * *